(12) United States Patent
Wu et al.

(10) Patent No.: US 12,209,291 B2
(45) Date of Patent: Jan. 28, 2025

(54) METHODS AND SYSTEMS FOR ANALYSIS OF SAMPLES CONTAINING PARTICLES USED FOR GENE DELIVERY

(71) Applicant: ProteinSimple, San Jose, CA (US)

(72) Inventors: Jiaqi Wu, San Jose, CA (US); Christopher Heger, Campbell, CA (US)

(73) Assignee: ProteinSimple, San Jose, CA (US)

( * ) Notice: Subject to any disclaimer, the term of this patent is extended or adjusted under 35 U.S.C. 154(b) by 0 days.

(21) Appl. No.: 18/493,087

(22) Filed: Oct. 24, 2023

(65) Prior Publication Data

US 2024/0052435 A1 Feb. 15, 2024

Related U.S. Application Data

(60) Division of application No. 18/087,772, filed on Dec. 22, 2022, now Pat. No. 11,827,946, which is a continuation of application No. 17/554,830, filed on Dec. 17, 2021, now Pat. No. 11,535,900, which is a continuation of application No. 17/466,916, filed on Sep. 3, 2021.

(51) Int. Cl.
| | | |
|---|---|---|
| C12Q 1/70 | (2006.01) | |
| C12N 15/86 | (2006.01) | |
| C12Q 1/00 | (2006.01) | |
| G16B 20/00 | (2019.01) | |
| G16B 40/00 | (2019.01) | |

(52) U.S. Cl.
CPC .............. *C12Q 1/70* (2013.01); *G16B 20/00* (2019.02)

(58) Field of Classification Search
CPC .......... C12Q 1/70; G16B 20/00; G16B 40/00; G01N 33/56983; G01N 27/44795
See application file for complete search history.

(56) References Cited

U.S. PATENT DOCUMENTS

| | | | |
|---|---|---|---|
| 5,002,582 A | 3/1991 | Guire et al. | |
| 6,087,188 A | 7/2000 | Johansen et al. | |
| 6,126,870 A | 10/2000 | Akhavan-Tafti | |
| 6,165,800 A | 12/2000 | Jiang et al. | |
| 6,254,634 B1 | 7/2001 | Anderson et al. | |
| 6,287,767 B1 | 9/2001 | Bronstein et al. | |
| 6,348,596 B1 | 2/2002 | Lee et al. | |
| 6,395,503 B1 | 5/2002 | Suzuki et al. | |
| 6,689,576 B2 | 2/2004 | Matsuno et al. | |
| 7,846,676 B2 | 12/2010 | Yang et al. | |
| 7,935,479 B2 | 5/2011 | O'Neill et al. | |
| 7,935,489 B2 | 5/2011 | O'Neill et al. | |
| 10,794,860 B2 | 10/2020 | Roach et al. | |
| 11,535,900 B1 | 12/2022 | Wu et al. | |
| 11,827,946 B2 | 11/2023 | Wu et al. | |
| 2006/0292558 A1 | 12/2006 | O'Neill | |
| 2007/0062813 A1 | 3/2007 | Gentalen et al. | |
| 2023/0075533 A1 | 3/2023 | Wu et al. | |
| 2023/0126263 A1 | 4/2023 | Wu et al. | |

FOREIGN PATENT DOCUMENTS

WO WO-2021144719 A1 7/2021

OTHER PUBLICATIONS

International Search Report and Written Opinion for Application No. PCT/US2022/075984, mailed on Dec. 5, 2022, 19 pages.
Kremser., L et al., "Capillary electrophoresis of viruses, subviral particles and virus complexes," Journal of Separation Science, vol. 30, No. 11, Jul. 1, 2007, pp. 1704-1713.
Kremser., L et al., "Labeling of capsid proteins and genomic RNA of human rhinovirus with two different fluorescent dyes for selective detection by capillary electrophoresis," Analytical Chemistry, Dec. 15, 2004, vol. 76, No. 24, pp. 7360-7365.
Li, T et al., "Determination of Full, Partial and Empty Capsid Ratios for Adeno-Associated Virus (AAV) Analysis," SciEx, Drug Discovery and Development, 2020, 5 pages.
Placidi, M et al., "ASGCT-2020 Annual Meeting | May 12-15, 2020 | Virtual Capillary Electrophoresis as a Tool to Assess Multiple Attributes of AAV Based Therapeutics," May 12, 2020, 1 page.
Placidi, M et al., "Capillary Electrophoresis as a Tool to Assess Multiple Attributes of AAV Based Therapeutics," Voyager Therapeutics, ASGCT-2020 Annual Meeting, May 12-15, 2020, 1 page.
Wang, C et al., "Developing an Anion Exchange Chromatography Assay for Determining Empty and Full Capsid Contents in AAV6.2," Mol Ther Methods Clin Dev., Sep. 26, 2019, vol. 15, pp. 257-263.

*Primary Examiner* — Barry A Chestnut
(74) *Attorney, Agent, or Firm* — COOLEY LLP

(57) ABSTRACT

Embodiments disclosed include systems, devices, and methods for analysis of samples containing particles used for gene delivery to determine a quality of the sample and/or an indication that the gene delivery particles are in a full, partial, and/or empty state. The present disclosure also relates to determining a protein and/or NA content in samples with known proportions of gene delivery particles in a full, partial, and/or empty state and based on the determination, establish a relationship between NA content and proportions of gene delivery particles in a full state. The present disclosure also relates to using such an established relationship to predict a proportion of the gene delivery particles in a full, partial, and/or empty state in test samples having the gene delivery particles in an unknown state.

23 Claims, 9 Drawing Sheets

10

METHODS AND SYSTEMS FOR ANALYSIS OF SAMPLES CONTAINING PARTICLES USED FOR GENE DELIVERY

CROSS-REFERENCE TO RELATED APPLICATIONS

This application is a divisional of U.S. Non-Provisional application Ser. No. 18/087,772, filed Dec. 22, 2022, entitled "METHODS AND SYSTEMS FOR ANALYSIS OF SAMPLES CONTAINING PARTICLES USED FOR GENE DELIVERY," which is a continuation of U.S. Non-Provisional application Ser. No. 17/554,830, filed Dec. 17, 2021, now U.S. Pat. No. 11,535,900, entitled "METHODS AND SYSTEMS FOR ANALYSIS OF SAMPLES CONTAINING PARTICLES USED FOR GENE DELIVERY," which is a continuation of U.S. Non-Provisional application Ser. No. 17/466,916, filed Sep. 3, 2021, entitled "METHODS AND SYSTEMS FOR ANALYSIS OF SAMPLES CONTAINING PARTICLES USED FOR GENE DELIVERY," the disclosures of each of which is hereby incorporated by reference in its entirety.

BACKGROUND

Some embodiments described herein relate to methods and systems for analysis of samples containing particles used for gene delivery. Some embodiments include methods and systems for quantification and/or prediction of amount of nucleic acid (NA) content in viral vectors in a sample.

Gene delivery systems, such as viral vectors and lipid nanoparticles, are commonly used to deliver target genes to biological systems for research and/or therapy. Adeno-Associated Viruses (AAVs), for example, are frequently used as viral vectors in gene therapies targeted to address human diseases. Currently, there are over 200 studies around the world conducting active clinical trials in Phase 1-3 that are directed to treating various conditions using gene therapies that leverage AAVs. AAVs, when used as gene delivery systems, can include plasmid DNA, which can be up to 5 kb in length; a gene of interest (GOI) can be inserted into the plasmid DNA. Production of AAVs for gene delivery includes a complex process of triple transfection of cells. The triple transfection process is targeted to incorporate three segments of nucleic acids (NA), namely: replication (rep), capsid (cap), and the GOI, to produce functional AAV particles. Partial transfection of a portion of the AAVs at any of the three steps of the triple transfection can result in a heterogeneity in the AAV particles that can be characterized by a 'full/empty' status of AAV particles. Said in another way, AAVs can exist as a heterogeneous population, giving a final sample that is, for example, 70% full (including the desired plasmid NA) and 30% empty (devoid of the desired plasmid NA). Empty or partially filled particles in a sample, when used for delivery of the GOI, can impact therapeutic efficacy, and thus can be unwanted biproducts of the manufacturing process. Assessment of samples for the empty/full status of AAV particles, however, can be laborious, challenging to implement, involve long purification processes, and/or include wastage of the sample that is to be tested. Efficient methods to assess the empty/full status of AAV particles and methods suitable for assessing the empty/full status of AAV samples in crude or unpurified samples are, however, currently lacking. Therefore, there exists a need for methods and systems for efficient assessment of samples containing particles for gene delivery.

SUMMARY

Some embodiments described herein relate to methods, systems, and apparatuses for analysis of samples containing particles used for gene delivery to determine a quality of the sample. The present disclosure also relates to determining a protein and/or NA content in samples with known proportions of gene delivery particles in a full, partial, and/or empty state and based on the determination, establish a relationship between NA content and proportions of gene delivery particles in a full state. The present disclosure also relates to using such an established relationship to predict a proportion of the gene delivery particles in a full, partial, and/or empty state in test samples having the gene delivery particles in an unknown state. In some implementations, disclosed embodiments can include generating one or more electronic identifiers associated with one or more samples and/or the gene delivery particles and/or composition of a sample. The electronic identifiers can be associated with an amount of NA content included in the gene delivery particles and/or a proportion of gene delivery particles in a sample that can be used to deliver a gene of interest into a biological environment for research and/or therapeutics purposes.

In some embodiments, a method includes introducing a sample containing a plurality of viral vectors in a conductive medium into a capillary, a first end of the capillary being ionically coupled to a first running buffer having a first pH, a second end of the capillary being ionically coupled to a second running buffer having a second pH such that a pH gradient is formed along the capillary. The method includes separating the plurality of viral vectors in the sample by applying a voltage between the first running buffer and the second running buffer. The method further includes incubating, after separating, the plurality of viral vectors with a selective binder configured to bind to a portion of a nucleic acid (NA) included in a subset of viral vectors from the plurality of viral vectors. The method further includes detecting a signal associated with the selective binder to determine at least one of (i) a quantity of the NA included in the subset of viral vectors from the plurality of viral vectors to which the selective binder is bound, or (ii) or an isoelectric point (pI) associated with the subset of viral vectors from the plurality of viral vectors that include the NA to which the selective binder is bound.

In some embodiments, a method includes introducing a plurality of samples into a plurality of capillaries, each sample from the plurality of samples including a different known proportion of Adeno-associated virus (AAV) vectors that include an amount of NA content. The method includes separating each sample from the plurality of samples using isoelectric focusing and labeling each sample from the plurality of samples in each capillary from the plurality of capillaries with a binder configured to bind to at least a portion of the specified DNA content. The method further includes detecting a signal associated with the antibody from each sample from the plurality of samples and determining a relationship between the signal from each sample and the known proportion of AAV vectors that include the specified NA content in that sample.

In some embodiments, a non-transitory processor-readable medium storing code representing instructions to be executed by a processor, includes instructions comprising code to cause the processor to receive a test signal associated with a test sample containing a plurality of viral vectors, the test signal being associated with a DNA content included in at least a subset of viral vectors from the plurality of viral vectors. The instructions further include code to cause the processor to extract a feature of the test signal that is configured to indicate a quantity of the DNA content of the subset of viral vectors from the plurality of viral vectors. The instructions further include code to cause the processor to compare the feature against a function that describes a relationship between (i) known features obtained from a plurality of signals, each signal from the plurality of signals detected from a standard sample from a plurality of standard samples, each standard sample containing a known proportion of viral vectors that include a specified amount of DNA content, and (ii) the known proportions of viral vectors that include the specified amount of DNA content contained in each standard sample from the plurality of standard samples. The instructions include code to cause the processor to determine, based on the comparison, a proportion of the plurality of viral vectors contained in the test sample that include a capsid and the specified DNA content.

DETAILED DESCRIPTION

Figure 1:
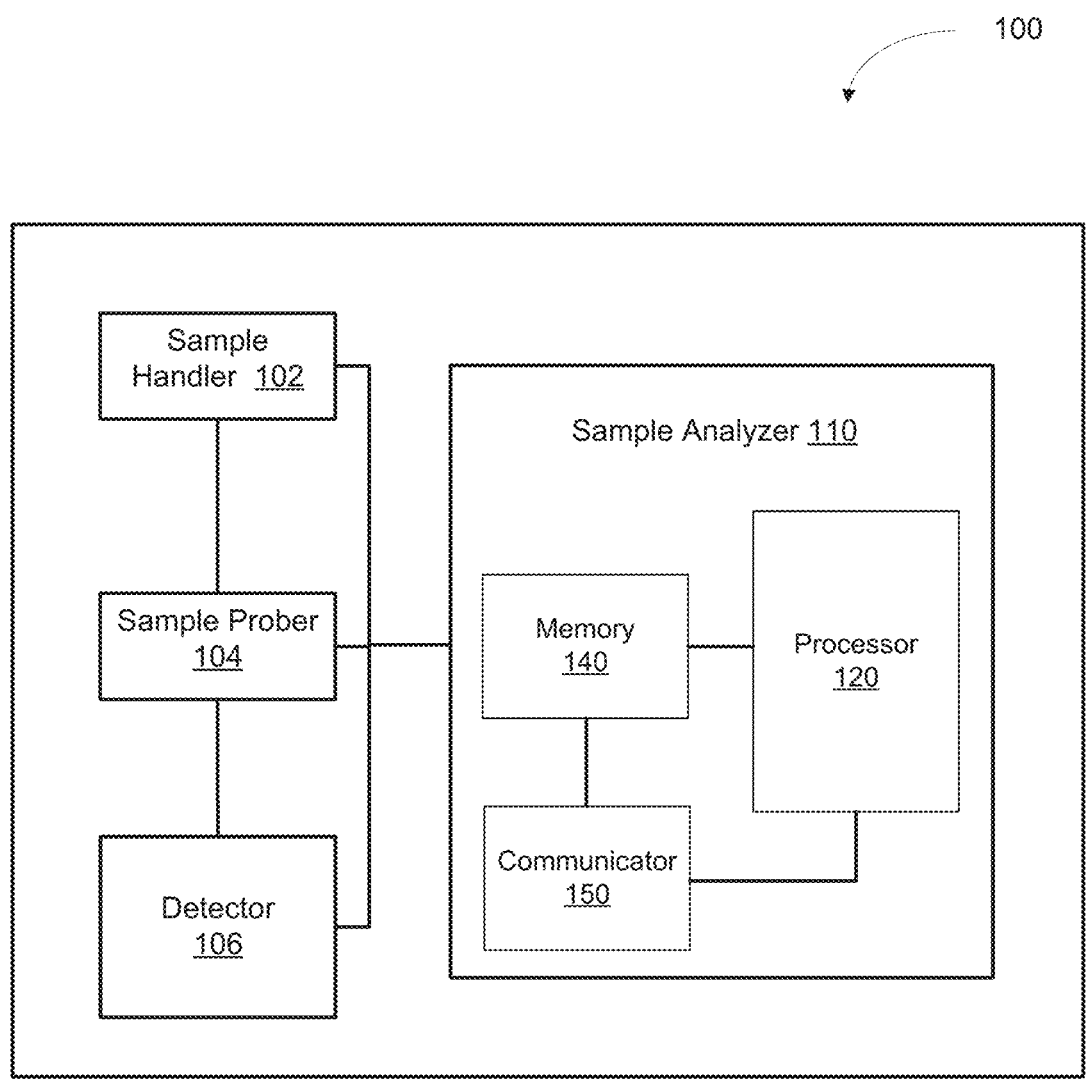
FIG. 1 is a schematic diagram of a system configured to analyze samples containing particles for gene delivery, according to an embodiment.

In some embodiments, a method includes introducing a sample containing a plurality of viral vectors in a conductive medium into a capillary, a first end of the capillary being ionically coupled to a first running buffer having a first pH, a second end of the capillary being ionically coupled to a second running buffer having a second pH such that a pH gradient is formed along the capillary. The method includes separating the plurality of viral vectors in the sample by applying a voltage between the first running buffer and the second running buffer. The method further includes incubating, after separating, the plurality of viral vectors with a selective binder configured to bind to a nucleic acid (NA) included in at least a subset of viral vectors from the plurality of viral vectors. The method further includes detecting a signal associated with the selective binder to determine at least one of (i) a quantity of the NA included in the subset of viral vectors from the plurality of viral vectors to which the selective binder is bound, or (ii) or an isoelectric point (pI) associated with the subset of viral vectors from the plurality of viral vectors that include the NA to which the selective binder is bound.

In some embodiments, a method includes introducing a plurality of samples into a plurality of capillaries, each sample from the plurality of samples including a different known proportion of Adeno-associated virus (AAV) vectors that include an amount of NA content. The method includes separating each sample from the plurality of samples using isoelectric focusing, and labeling each sample from the plurality of samples in each capillary from the plurality of capillaries with a binder configured to bind to at least a portion of the specified DNA content. The method further includes detecting a signal associated with the binder from each sample from the plurality of samples and determining a relationship between the signal from each sample and the known proportion of AAV vectors that include the specified NA content in that sample.

In some embodiments, a non-transitory processor-readable medium storing code representing instructions to be executed by a processor, includes instructions comprising code to cause the processor to receive a test signal associated with a test sample containing a plurality of viral vectors, the test signal being associated with a DNA content included in at least a subset of viral vectors from the plurality of viral vectors. The instructions further include code to cause the processor to extract a feature of the test signal that correlates to a quantity of the DNA content of the subset of viral vectors from the plurality of viral vectors. The instructions further include code to cause the processor to compare the feature against a function that describes a relationship between (i) known features obtained from a plurality of signals, each signal from the plurality of signals detected from a standard sample from a plurality of standard samples, each standard sample containing a known proportion of viral vectors that include a specified amount of DNA content, and (ii) the known proportions of viral vectors that include the specified amount of DNA content contained in each standard sample from the plurality of standard samples. The instructions include code to cause the processor to determine, based on the comparison, a proportion of the plurality of viral vectors contained in the test sample that include a capsid and the specified amount of DNA content.

Systems, methods, and apparatuses of the disclosure relate to the analysis of a sample containing a mixture of particles configured for gene delivery, also referred to as "gene delivery particles" or "GD particles". The present disclosure can also be useful in performing quantitative analysis of samples containing GD particles configured to deliver target genes into a biological environment. While referred to herein as "gene delivery particles", in some embodiments, the particles described can be used for delivery of any suitable payload (including non-genetic material) such as inorganic material, xenobiotics, pharmaceutical products, and/or the like. The system, methods, and apparatuses, while described to relate to analysis of samples containing "gene delivery particles", in some embodiments, can just as well be used to analyze samples containing particles used for delivery of any suitable payload (including genetic and/or non-genetic material) such as inorganic material, xenobiotics, pharmaceutical products, and/or the like.

As described herein, gene delivery is the process of introducing foreign genetic material including nucleic acids (NA), such as deoxyribonucleic acid (DNA) or ribonucleic acid (RNA), into host cells. The foreign genetic material that is introduced can be configured such that upon gene expression in the host cell, the host cell can generate target products like proteins that may serve a desired goal. Successful gene delivery includes delivery of a portion of a NA (e.g., a gene which can include a sequence of nucleotides in DNA or RNA that encodes the synthesis of a gene product, either RNA or protein) into a host cell. The delivery is such that the portion of NA can either integrate into the genome or replicate independently of it. In some implementations, a target NA or transgene can be synthesized as part of a recombinant vector NA (e.g., a plasmid), which can be designed to carry the transgene as a payload within a vector particle or gene delivery particle, enter the desired host cell, and deliver the transgene to that cell's genome or intracellular space. Delivery vectors or gene delivery particles ("GD particles") utilized for gene delivery include recombinant viruses and synthetic particles that may be of viral (e.g., synthetic viruses, attenuated viruses) and/or non-viral origin (e.g., lipid nanoparticles).

Adeno-associated viruses (AAVs) are an example of viral particles that serve as a powerful gene therapy delivery tool. Currently, there are over 200 therapies in Phase 1-3 of clinical trials that leverage recombinant AAV particles to deliver desired transgenes. Recombinant AAVs have a plasmid (up to 5 kb) with the gene of interest inserted. The production of functional AAV particles to be used for gene delivery involves triple transfection of host cells with three plasmids—replication (rep), capsid (cap), and the gene of interest (GOI). Following transfection the viral particles can be considered to be in a full status if they successfully include the three plasmids, and partial or empty if they lack of at least one or all of the plasmids, respectively. This process of production of viral particles for gene delivery can and often does lead to heterogeneity in samples containing mixtures of viral particles that have full, partial, and empty statuses. Thus, recombinant AAV particles, or any other GD particles, in samples used for gene delivery can exist as a heterogeneous population, giving a sample that is, for example, 70% full, 30% empty. Empty or partially filled GD particles impact therapeutic efficacy, and thus can be unwanted biproducts of the manufacturing process. Therefore, it can be useful for manufacturers to examine production batches of sample with GD particles to quantify each sample for the proportion of GD particles that may be in the full, partial, and/or empty state, and set release criteria based on the quantification. For example, samples with GD particles of which at least or more than 50% are in the full state might be considered acceptable for a certain application. Conversely, for certain applications, a sample containing less than 50% full AAVs (or any other suitable threshold depending on the application) may be unacceptable. Accordingly, it can be desirable to evaluate the proportion of full AAVs in heterogenous samples early in the complex and expensive production process.

Currently available methods to assess the empty/full status of heterogenous populations of GD particles are challenging to implement in quality control (QC), involve usage of relatively large quantities of the sample to be tested, call for high levels of expertise. These conventional methods include analytical ultracentrifugation (AUC) and transmission electron microscopy (TEM). In addition to the above listed challenges, these methods require relatively pure samples—thus requiring long purifications prior to assessment of the empty/full status of GD particles. Methods to assess empty/full status earlier in the GD particle production process are not well developed. There is a need for methods and systems for efficient assessment of samples with GD particles, including samples that may be crude and/or unpurified.

The embodiments described herein include a method for determination of NA content and/or protein content associated with intact GD particles (e.g., assembled recombinant AAV particles) in crude samples before substantial purification, thus providing an advantage of ability to analyze samples for the relative proportion of particles in the empty, partial, and/or full state using in-process, crude samples.

In some embodiments, the methods disclosed herein can be performed using instrumentation configured for separation of analytes using methods such as isoelectric focusing (IEF) or capillary IEF. Techniques such as IEF can be a powerful approach to separating analytes in a sample, for example, charge variants associated with GD particles, with good resolution and sensitivity. IEF can be performed by applying a voltage to a separation medium having a pH gradient and containing the sample. For example, opposite ends of the separation medium can be ionically coupled to reservoirs containing buffers having a first pH (e.g., an acid) and a second pH (e.g., a base). Under an applied electric field, each charged component of the sample (e.g., each GD particle) migrates to a position along a pH gradient, where the pH is the same as that component's isoelectric point (pI). Capillary isoelectric focusing (CLEF) is a variant of this approach where IEF is performed in a sample held in a lumen of a capillary. In case of CLEF, due to the miniaturized fluidic path and insignificant Joule heating involved, larger magnitude electric fields can be applied for the separation of components in a sample held in the lumen of a capillary, resulting in fast separation and better resolution of separation of the analytes in the sample. In some implementations a significant portion of the capillary can be imaged during and/or after separation, in a process called imaging capillary isoelectric focusing (iCIEF) or "whole" column imaging capillary isoelectric focusing, which is described in U.S. Pat. No. 10,794,860 entitled, "Systems and methods for capillary electrophoresis, isoelectric point, and molecular weight analysis," filed on Jul. 12, 2018, the disclosure of which is incorporated herein by reference in its entirety.

Following separation, the sample can be examined using immunoassays with targeted detection of moieties using selective binders (e.g., antibodies) with suitable labeling (e.g., fluorescent, luminescent label, etc.) that can be identified and/or recorded using established methods of photo detection or image-based detection. Immunoassays with targeted detection of moieties also offer specificity in the form of targeted detection of desired NA and/or protein content. This provides an additional advantage of cross-platform compatibility and ability for implementation agnostic of instrumentation, along with specificity in quantitative analyses. In some implementations, the methods described allow quantitative analysis of relatively unpurified samples to determine an amount of specific NA and/or protein content, which is otherwise not possible using currently available techniques.

Embodiments described herein include apparatus, methods, and systems for performing analysis of samples containing GD particles using a suitable separation technique (e.g., capillary isoelectric focusing) followed by immobilization and immunoassay such that there is streamlined, semi-automatic, separation, labeling, visualization, detection, and/or quantification of a proportions of functional GD particles in samples with heterogenous mixtures of GD particles.

Additionally, in some implementations, the methods disclosed enable determining a relationship between NA content and/or protein content of a sample and a proportion of GD particles in full, partial, and/or empty state in the sample. Moreover, the methods described enable the prediction of a proportion of GD particles that may be full, partial, and/or empty in a heterogenous mixture of GD particles in an unknown sample, based on the relationship between the NA content and/or the protein content of samples and proportion of GD particles in full, partial, and/or empty state in the samples.

Definitions

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" mean plus or minus 10% of the value stated and all values in between. For example, about 0.5 would include 0.45 and 0.55, about 10 would include 9 to 11, about 1000 would include 900 to 1100. The term "substantially" when used in connection with shape relationships (e.g., linear, cylindrical, etc.), structural relationships (e.g., perpendicular, etc.), and/or other geometric relationships is intended to convey that the structure so defined is nominally linear, cylindrical, perpendicular, and/or the like. As one example, a portion of a support member that is described as being "substantially linear" is intended to convey that, although linearity of the portion is desirable, some non-linearity can occur in a "substantially linear" portion. Such non-linearity can result from manufacturing tolerances, or other practical considerations (such as, for example, the pressure or force applied to the support member). Thus, a geometric construction modified by the term "substantially" includes such geometric properties within a tolerance of plus or minus 5% of the stated geometric construction. For example, a "substantially linear" portion is a portion that defines an axis or center line that is within plus or minus 5% of being linear.

As used herein the term "module" refers to any assembly and/or set of operatively-coupled electrical components that can include, for example, a memory, a processor, electrical traces, optical connectors, software (executed in hardware), and/or the like. For example, a module executed in the processor can be any combination of hardware-based module (e.g., a field-programmable gate array (FPGA), an application specific integrated circuit (ASIC), a digital signal processor (DSP)) and/or software-based module (e.g., a module of computer code stored in memory and/or executed at the processor) capable of performing one or more specific functions associated with that module.

As used herein, the terms "analyte" and/or "target analyte" refer to any molecule or compound to be separated and/or detected with the methods, apparatus and systems provided herein. Suitable analytes include, but are not limited to, small chemical molecules such as, for example, genetic material, pharmaceutical molecules, clinical molecules, inorganic molecules, and/or biomolecules. More specifically, such chemical molecules can include, but are not limited to toxins, therapeutic and/or drugs, antibiotics, organic materials, hormones, antibodies, antibody fragments, antibody-molecule conjugates (e.g., antibody-drug conjugates), antigens, cellular membrane antigen, proteins (e.g., enzymes, immunoglobulins, and/or glycoproteins), nucleic acids (e.g., DNA and/or RNA), proteins, capsids, lipids, lectins, carbohydrates, viruses, glycoproteins, metabolites, cofactors, nucleotides, polynucleotides (comprising ribonucleic acid and/or deoxyribonucleic acid), transition state analogs, inhibitors, receptors, receptor ligands (e.g., neural receptors or their ligands, hormonal receptors or their ligands, nutrient receptors or their ligands, and/or cell surface receptors or their ligands), receptor-ligand complexes, nutrients, electrolytes, growth factors and other biomolecules and/or non-biomolecules, as well as fragments and combinations thereof. In some embodiments, the analyte is a protein or a protein complex encapsulating nucleic acid content, and the sample is a cellular lysate or a purified protein. Other suitable analytes can include nanoparticles (e.g., lipid nanoparticles), lipid aggregates, agglomerates, floc, and/or dispersed phase droplets or particles of colloids and/or emulsions.

As used herein, the term "sample" refers to a composition that contains an analyte or analytes to be detected. A sample, in some embodiments, is heterogeneous, containing a variety of components (e.g., different types of particles or particles in various states) or homogenous, containing one component (e.g., a population of one type of particle, or particles in one type of state). In some instances, a sample can be naturally occurring, a biological material, and/or a manufactured or synthetic material. Furthermore, a sample can be in a native (e.g., a cell suspension) or denatured form (e.g., a lysate). In some instances, a sample can be a single cell (or contents of a single cell, e.g., as a cellular lysate from the single cell, or a purified protein) or multiple cells (or contents of multiple cells, e.g., as a cellular lysate from the multiple cells, or a purified protein from the multiple cells). In some instances, a sample can be from a living organism, such as a eukaryote, prokaryote, mammal, human, yeast, and/or bacterium or the sample can be from a virus or a modified (e.g., attenuated) virus.

In some embodiments, the sample is a heterogeneous biological sample or derived from a heterogeneous biological sample, for example a tissue lysate, a cellular lysate or a mixture of biomolecules such as proteins (e.g., a purified protein). In a further embodiment, a protein within the cellular lysate is the analyte to be detected by the methods and systems described herein. In a further embodiment, the apparatus, systems, and methods provided herein provide for the detection of a particular form of a protein, for example, a capsid protein. The cellular lysate, for example, can be the lysate of one cell or a mixture of cells. Moreover, the cellular lysate can include a single cell type, or multiple cell types. The cell type, in some embodiments, includes a stem cell or a cancer cell, or a population of stem cells, or a population of cancer cells. In some embodiments, a sample comprises one or more stem cells (e.g., any cell that has the ability to divide for indefinite time periods and to give rise to specialized cells) and/or stem cell lysates. Suitable examples of stem cells can include but are not limited to embryonic stem cells (e.g., human embryonic stem cells (hES)), and non-embryonic stems cells (e.g., mesenchymal, hematopoietic, induced pluripotent stem cells (iPS cells), or adult stem cells (MSC)).

As used herein, the terms "standard" and/or "internal standard" refer to a well-characterized substance of known amount and/or identity (e.g., known isoelectric point, molecular weight, electrophoretic mobility profile, number of base pairs in the case of a nucleic acid, molecular composition, etc.) that can be added to a sample comprising the analyte, for comparative purposes. In some embodiments, a known quantity of standard is added to a sample comprising one or more analytes, and both the standard and the molecules in the sample, including the analyte(s) are separated on the basis of isoelectric point by electrophoresis). A comparison of the standard and analyte signal then provides a quantitative or semi-quantitative measure of the amount of analyte originally present in the sample.

In general, isoelectric focusing (IEF) standards are known based on established isoelectric point. Similarly, molecular weight standards are known. In some instances, the standard and/or the analyte(s) can be detected with one or more detection molecules or reagents, such as with an antibody against the analyte or a labeling moiety attached to the standard. In some embodiments, a primary antibody is used to bind the target analyte (e.g., a GD particle), and a secondary antibody conjugated to a fluorescent or a chemiluminescent reagent is introduced to bind the primary antibody or the primary antibody-analyte complex. The signal of the fluorescent or chemiluminescent molecule is then detected. In other instances, the standard and/or the analyte(s) can be detected via native fluorescence (e.g., via fluorescence of tryptophan amino acids within the standard and/or analyte(s)) and/or absorbance. The signal of the standard and the signal of the analyte(s) can then be compared to measure the concentration of the analyte(s) in the sample. In addition or alternatively, a relevant characteristic of the analyte (e.g., isoelectric point, molecular weight, etc.) can be determined by comparison to the standard.

In some embodiments, an internal standard can be a purified form of the analyte itself, which is generally made distinguishable from the analyte in some way. Any method of obtaining a purified form of the analyte can include but is not limited to purification from nature, purification from organisms grown in the laboratory (e.g., via chemical synthesis), and/or the like. The distinguishing characteristic of an internal standard can be any suitable change that can include but is not limited to dye labeling, radiolabeling, or modifying the mobility of the standard during the electrophoretic separation so that it is distinguishable from the analyte. For example, the analyte and the internal standard can each be labeled with fluorescent dyes that are each detectable at discrete emission wavelengths, thereby allowing the analyte and the standard to be independently detectable. In some instances, an internal standard is different from the analyte but behaves in a way similar to or the same as the analyte, enabling relevant comparative measurements. In some embodiments, a standard that is suitable for use can be any of those described in U.S. Patent Application Publication No. 2007/0062813 entitled, "Electrophoresis Standards, Methods and Kits," filed on Sep. 20, 2006, the disclosure of which is incorporated herein by reference in its entirety. For example, in some embodiments, the multiple analytes are a population of GD particles which may be viral vectors with specific capsid proteins or a subpopulation of capsid proteins. In this regard, it may not be practical to include a single internal standard corresponding to each of the individual proteins of the population of proteins or subpopulation of proteins. Accordingly, in some embodiments, a general isoelectric point standard is introduced into the systems and apparatus provided herein. The standard, in some embodiments, can be a ladder standard operable to identify different isoelectric points along the capillary tube. Proteins in the sample that migrate during the electrophoresis are compared to the ladder to determine the isoelectric point of the proteins present in the sample. In some embodiments, ladder standards are used.

Embodiments described include systems and methods to perform separation, detection, and/or quantitative analysis of heterogenous populations of GD particles in a sample (e.g., based on molecular weight and/or isoelectric point) to determine their full, partial, or empty status. The sample can be prepared in a conductive medium and loaded into capillary that is in turn loaded into a sample analysis system as described herein.

FIG. 1 shows a schematic of an example sample analysis system 100. In some embodiments, the sample analysis system (also referred to here as "the analysis system" or simply "the system") will allow users to quantitively analyze a sample containing a heterogenous mixture of GD particles to determine a proportion of GD particles that may be in a full, partial, and/or empty state. The system 100 can allow users to example samples with specific types of GD particles and establish relationships between NA content and/or protein content in the samples and a known concentration of the GD particles in the full, partial, and/or empty state in the samples. The system 100 can allow examination of test samples with GD particles of the specific type but in unknown states and, based on established relationships, predict the proportions of GD particles in the test sample that may be in the full, partial, and/or empty state. The system 100 can support quantitative analyses using a combination of separation and immunoassay using one or more types of selective binders such as detection binders and/or capture binders that take advantage of markers that are expected to be found on GD particles in the sample.

The system 100 includes a sample handler 102, a sample prober 104, a detector 106, and a sample analyzer 110 (also referred to as the analyzer). The various components of the system 100 can be interconnected in any suitable manner (physically, fluidically, electrically, and/or communicatively, e.g., through wired or wireless connection methods). In some embodiments, the analyzer 110 can be physically collocated with the sample handler 102, sample prober 104 and/or detector 106 (e.g., disposed in the same room or within a common housing). In other embodiments, the analyzer 110 can be an enterprise system at least partially hosted in an enterprise server, such as, for example a web server, an application server, a proxy server, a telnet server, a file transfer protocol (FTP) server, a mail server, a list server, a collaboration server and/or the like. Although not shown in FIG. 1, the system 100 can be configured to be coupled to one or more other external computing entities (e.g., personal computers, servers, cloud servers, etc., which may include a processor and a memory) in any suitable manner though a communication network or a communication channel. For example, the analyzer 110 can be partially and/or completely implemented using an external computing entity.

The sample handler 102 can include one or more containers that can be configured to house, hold, carry, convey, or otherwise suitably handle the sample. In some embodiments, the container can be a capillary, a column, wet plate, a microwell, a vial, a well, and/or any other suitable container configured to support separation and analysis of the sample as described herein. In some embodiments, the container can be a capillary that includes a lumen through which a fluid path can be defined. In some embodiments, the sample handler 102 can be configured to include a cartridge retainer configured to engage with a cartridge that in turn is configured to hold a capillary. In some embodiments, the sample handler 102 can include one or more reservoirs to hold running buffers (e.g., acids, bases, and/or the like) or other suitable fluids used for sample handling, separation of analytes, immobilization of analytes, assaying one or more analytes, and/or visualization and detection of analytes. The sample handler 102 can be configured to receive the medium in the one or more containers from any suitable source. For example, the sample handler 102 can include a syringe, nozzle, reservoir, a vacuum sources, a pressure source, and/or any other suitable fluid handling device(s) operable to transfer the sample from a sample reservoir as a source an into the container which can be a column, capillary and/or the like.

In some embodiments, the sample handler 102 can be configured such that the capillary is housed with respect to the one or more running buffers such that a pH gradient can be formed through a lumen of the capillary with a first end of the capillary fluidically coupled to a first running buffer at a first pH and a second end of the capillary fluidically coupled to a second running buffer at a second pH different from the first pH, the pH gradient extending between the first pH and the second pH.

In some embodiments, the sample handler 102 can include suitable electrical contact points or connections configured to be electrical connection with a power source (e.g., a power source included in the system 100 or an external power source) and to provide electrical access to the contents in the lumen of the capillary holding the sample in an electrically conductive medium. The sample handler 102 can be configured to provide an applied electric field across the sample held in the conductive medium in the lumen of the capillary to cause a separation of the contents or analytes in the sample including GD particles in the sample based on their respective isoelectric points along the pH gradient formed within the lumen of the capillary. In some embodiments, the sample handler 102 can be configured such that upon applying the electric field the GD particles focus based on their isoelectric points and stay intact such that the NA content within the GD particles is retained within the GD particles. Said in another way, in some embodiments, the separation of the GD particles and the associated proteins and NA content is such that NA that is encapsulated by GD particles remains within the GD particles and focuses along the pH gradient upon application of external electric field based on the pI of the protein (e.g., capsid protein) or encapsulating portion of the GD particle. In some implementations, the sample handler 102 (the pH gradient, and/or the capillary) can be configured such that non-encapsulated NA (i.e., NA not contained within a GD particle or capsid) can be cleared away without being focused in the pH gradient (e.g., due to having a low pI that may be outside the range defined within the capillary). In some implementations, the system 100 and the methods described herein may be superior to analysis of samples using processes like enzyme linked immunosorbent assay (ELISA) in which analytes are not isolated before being probed with binders and/or detection agents.

In some embodiments, the sample handler 102 can be further operable to immobilize a heterogeneous mixture of GD particles in a sample in the medium held in the capillary while allowing a fluid path. In some embodiments, the sample can be prepared in a medium that includes an activatable component (e.g., photoactivatable, heat activatable, and/or the like) that can be used to immobilize the contents of the sample in the fluid path in the capillary. The sample handler 102 can include a mixing vessel, agitator, heat source, light source, and/or any other suitable sample and/or fluid handling devices operable to allow immobilization of the sample held in the capillary or plate as desired. In some implementations, the immobilization can be performed following the separation of analytes using isoelectric focusing such that GD particles are focused and immobilized at a location in the capillary based on their isoelectric points. In some embodiments, the sample handler 102 can be configured to provide proteases or other suitable reagents to disrupt the GD particles in the capillary to provide an access to the NA content that may be encapsulated, for example by a capsid protein. In some embodiments, the immobilization of the GD particles can be sufficient to provide access to the NA content that may be encapsulated, without the need for a separate disruption step.

The sample handler 102 can, in some embodiments be operable to introduce a detection agents or binders that can be used to selectively bind to one or more components of the GD particles or other desired analytes in the capillary. As discussed in further detail below, the binders can include antibodies targeted to bind to NA or proteins that are to be quantified using the systems and methods described herein. Binders can be configured for selectively binding to one component but not others (e.g., NA but not proteins or vice versa). Binders can be configured to be selectively binding to one component, but non-specific and binding to all species of that component (e.g., all NA, all proteins, etc.). In some instances, one or more binders can be configured for selective binding that is also specific binding. Said in another way, the binders can be configured to selectively bind to one component and specifically bind to only certain species of that component (e.g., specific proteins, specific NA sequences, etc.).

One or more of the binders can include a label (e.g., a fluorescent tag, or a chemiluminescent label) that can be used to detect and/or quantify the presence of the binder indicating the presence of the targeted NA or protein. In some embodiments, the sample handler 102 can include one or more viewing windows or apertures configured to interface between the sample handler 102 and the sample prober 104 and/or the detector 106. In some embodiments, the sample holder 102 can include a viewing window in a cartridge holding the capillary that is used to separate, immobilize, and/or analyze a sample such that the lumen of the capillary can be accessed by the sample prober 104 and the detector 106. As an example, the viewing window can include a substantially long aperture along the length of the capillary such that the lumen of the capillary including the GD particles that may be separated, immobilized, and/or labeled can be illuminated with light of a specified range of wavelengths and the emitted signals (e.g., fluorescence, chemiluminescence, etc.) emitted along the pH gradient formed in the lumen of the capillary (e.g., following separation by cIEF) can be captured in the form of an image and/or video. In some embodiments, the viewing window can be localized to a distal portion of the capillary such that contents of the capillary are mobilized to travel through the capillary, across the portion of the capillary adjacent to and accessible via the viewing window, and be ejected out from a distal end of the capillary.

The sample prober 104 can include a light source that is configured to illuminate the capillary using light of a specified wavelength to invoke emitted signals from specific groups of binders that may be configured to selectively bind to one or more NA or proteins or otherwise detect the one or more NA or proteins. In particular, the light source in the sample prober 104 can be configured to emit one or more pre-determined optical signals configured to excite a dye, label, or other suitable marker bound to or otherwise associated with binders (e.g., antibodies, capture binders, etc.). The binders can be chosen to be targeted to bind to specific components in GD particles. For example, different binders can be configured to selectively bind to surface proteins on capsids or encapsulating portions of GD particles (e.g., proteins VP1, VP2, VP3 that occur on capsids of AAV vectors). As another example, different binders can be configured to selectively bind to NA (e.g., anti-DNA antibodies that selectively bind to DNA). In some implementations, the binders can be chosen to non-specifically bind to a desired type of NA content (e.g., a pan-DNA or a pan-RNA antibody). In some implementations, the binders can be chosen to specifically bind to a desired type of NA content (e.g., a specific DNA or a sequence). As an example, in some instances, the binder can be chosen to specifically bind to NA content associated with a source and not to other NA. For example, the binder can be chosen to bind to a ssDNA associated with a virus or a NA sequence associated with a payload. In some instances, binders can be chosen to target dsDNA, and/or a host DNA. In some instances, one or more binders can be chosen to distinguish between GD particles and contaminants, for example, based on binders that target payload NA compared against binders that target host NA. In some instances, even more targeted binding to specific segments of nucleotides can be effected to detect and or identify the presence of the specific segments of nucleotides. In some instances, selective binders that are non-specific (bind to all species of a component) can be used in conjunction with selective binders that are specific (bind to only a sub species of a component). For example, segments of complementary NA sequences can be tagged with additional binders (e.g., antibodies) to bind to target sequences in the NA content in GD particles. In some implementations, the segments of complementary NA sequences can be designed to detect and bind to NA that provide a specified degree of match (e.g., a 10%, 20%, 30%, 40%, 50%, 60%, 70%, 80%, 90%, or 100% or any percentage value therebetween). In some implementations, a complementary DNA can be a primary binder targeting a specific NA sequence, an antibody configured to bind to the complementary DNA can be a secondary binder, and a tertiary antibody, tagged with a label, can be used to bind to the secondary binder.

The binders can be configured to respond to excitation by light of different wavelengths. The response can be in a form that can be recorded as an optical signal. For example, the binders can be excited by different wavelengths of light emitted by the light source in the sample prober 104 and respond in the form of an optical signal in a set of wavelengths of light (e.g., absorbance, chemiluminescence, fluorescence, etc.). In some embodiments, one or more binders can be configured to selectively bind to different moieties, each of the one or more binders having different excitation bands that respond to light of different wavelength (or range of wavelengths). The sample prober 104 can include one or more lights sources to provide light of desired wavelength or range of wavelengths for a desired excitation of the one or more binders. In addition, or alternatively, the light source in sample prober 104 can be operable to emit a broad spectrum (e.g., white light) that can be absorbed and/or reflected, by the one or more binders.

The detector 106 can include an optical detector (e.g., a charge-coupled device, a photodiode, a camera, and/or suitable optics). In some embodiments, the detector 106 can further include memory operable to record data associated with signals detected by the optical detector and/or a processor operable to process such data. The detector 106 can be operable to image the capillary (or multiple capillaries), for example, capture an image of the capillary (or multiple capillaries), including substantial portions of the lumen of the capillary that hold separated and/or immobilized GD particles bound to binders with labels, and/or capture individual images of each capillary or portions of a capillary. The detector 106 can further be operable to detect optical signals emitted or reflected by labels associated with GD particles within the capillaries, NA, and/or protein content associated with the GD particles. For example, the detector 106 can be operable to detect fluorescent or other emissions of markers bound to or otherwise associated with binders that are in turn associated with NA or protein content in GD particles. In instances where different populations of GD particles, NA segments (e.g., DNA or RNA segments), and/or proteins have different markers or labels associated with them, the detector 106 and/or the sample analyzer 110 can be operable to detect different signals from each population, thereby distinguishing different types of binders, and hence different subpopulations of GD particles, NA segments, proteins, specifically targeted analytes, and/or the like.

As illustrated in FIG. 1, the analyzer 110 includes a communicator 150 operable to receive signals from and/or transmit signals to the detector 106, the sample prober 104, and/or sample handler 102 via any suitable wired or wireless technology. For example, the detector 106 can be operable to transmit raw data to the analyzer 110, which can be operable to process and/or otherwise analyze the raw data using the processor 120 and the memory 140. It should be understood however, that in some embodiments, some or all processing of optical signals detected by the detector 106 can be performed by the detector 106 itself. Similarly stated, the analyzer 110 may be physically co-located with the detector (e.g., in a single housing) and/or the detector 106 can include a processor and a memory and be operable to perform partial or pre-processing of optical data. The analyzer 110 can be located proximate to the detector 106, for example, as part of a single instrument in a single housing or located in the same room or building as the detector 106. Alternatively, the analyzer 110 can be remote from the detector 106 such that at least a portion of data analysis can be performed remotely (e.g., off site and/or in a private or commercial cloud computing environment).

The detector 106 and/or the analyzer 110 can be operable to identify a presence and/or quantify an amount of a targeted NA and/or protein associated with GD particles that have been separated, for example, based on their isoelectric point. For example, the presence of specific proteins can be detected using protein specific antibodies that can be tagged directly or indirectly (via a secondary antibody) with a label or marker. The presence of NA content encapsulated in GD particles (e.g., gene of interest, DNA segments, RNA segments, host DNA, etc.) can be detected and/or quantified by using DNA specific antibodies that can be tagged directly or indirectly (via a secondary antibody) with a label or marker. In some embodiments, specific segments of NA (e.g., oligonucleotides with a particular nucleotide sequence) included in GD particles can be targeted by providing suitable binders (e.g., binders that specifically target and selectively bind to the targeted segment based on the nucleotide sequence, for example, using a complementary sequence). In addition, or alternatively, labels or markers bound to or otherwise associated with NA and/or protein components in GD particles can be detected by fluorescence, phosphorescence, absorbance, chemiluminescence, or any other suitable technique. Similarly stated the binders or associated markers (e.g., labels tagged on binders) can be illuminated by the light source in the sample prober 104 and detected by the detector 106 and/or the analyzer 110 based on optical signals emitted, absorbed, scattered, or otherwise altered by the binders and/or associated markers. Binders and/or other markers can be operable to generate different signals associated with different bound components (e.g., NA, protein, NA segment, protein type, etc.) which may be associated with subpopulations of GD particles.

The detector 106 and/or the analyzer 110 can be operable to detect the different signals associated with different bound components and distinguish the different the sub populations of components associated with the GD particles based on such signals and their source based on the localization of the GD particles following separation, for example, via isoelectric focusing. As described previously, in some implementations, the sample handler 102 (the pH gradient, and/or the capillary) can be configured such that non-encapsulated free NA (i.e., NA not contained within a GD particle or capsid) can be cleared away without being focused in the pH gradient (e.g., due to having a low pI that may be outside the range defined within the capillary) and thus not be detected by the detector 106 and/or the analyzer 110.

The detector 106 and/or the analyzer 110 can be operable to quantitate signals obtained from by extracting features from the signals that are configured to indicate a quantity associated with the binders emitting the signal and a quantity associated with the NA or protein content that the binders may be bound to. As an example the feature can includes a peak of the signal, an area under the curve associated with the signal (e.g., a cumulative area under the curve within a specified range of isoelectric points), one or more isoelectric points associated with one or more peaks in the signals, and/or the like. In some embodiments, the detector 106 and/or the analyzer 110 can be configured to distinguish or isolate one or more populations of GD particles based on identifying an isoelectric point associated with a peak in the signal. In some embodiments, the analyzer 110 can obtain a first set of signals indicating a quantity and/or isoelectric point associated with NA content in GD particles in a sample from a given source and a second set of signals indicating a quantity and/or isoelectric point associated with protein content in GD particles in sample from the same source. The analyzer 110 can be configured to analyze the first set of signals to determine a quantity of NA content in GD particles in the sample and analyze the second set of signals to determine a quantity of protein content in the sample. In some embodiments, the first set of signals to determine a quantity of NA content in GD particles in the sample and the second set of signals to determine a quantity of protein content in the sample can be correlated to associated the protein content with the NA content. In some embodiments, the samples to determine the quantity of NA and the quantity of protein can be the same sample. In some embodiments, the samples to determine the quantity of NA and the quantity of protein can be different samples obtained from the same source and examined in one or more capillaries in parallel or in sequential order. The analyzer 110 can be configured to compare the first set of signals with the second set of signals to determine a proportion of GD particles in that sample that may be in a full, partial, and/or empty state.

As described previously, the analyzer 110 can be configured to examine a set of known samples, for example, well characterized samples with known and varying proportions of GD particles of a specified type in the full or empty state. Based on the examination of signals (e.g., signals associated with NA content and/or protein content) obtained from the examination of well characterized samples the analyzer 110 can establish a relationship between features extracted from the signals and the known proportions of GD particles in the full/partial/empty state. The analyzer 110 can then be configured to examine signals from an unknown test sample that has a heterogenous mixture of GD particles of the same specified type but with an unknown proportion in a full, partial, and/or empty state, and based on the relationship, predict the proportion of GD particles in the full, partial, and/or empty state in the test sample.

In some embodiments, the sample handler 102 can be operable to introduce detection binders into the capillaries. The sample handler 102 can be operable to introduce detection binders before or after the separation and/or immobilization of GD particles. As discussed in further detail herein, detection binders can be operable to selectively bind to a subgroup of NA and/or protein components and/or an analyte associated with GD particles. Detection binders can further be operable to be excited by the light source in the sample prober 104 and/or detected and analyzed by the detector 106 and/or the analyzer 110. In some instances, the sample handler 120 can introduce a protease, a lysing agent, or other suitable agent to disrupt the GD particles after the GD particles are separated and/or immobilized and before detection binders are introduced, imaged, and/or analyzed. The processing of the sample in the sample handler 120 can be such that the GD particles are substantially intact and the NA content of the GD particles remains within the GD particles and focuses or separates along with the respective GD particles (e.g., capsid protein of AAVs). In some instances, the processing of the sample in the sample handler 120 can be such that it suitably impacts the GD particles (e.g., provides cracks or access points on the encapsulation, capsid, or the like) such that the access points permit detection binders specific for NA (e.g., anti-DNA antibodies) to enter into the GD particles (e.g., capsids) and bind to the NA content that may be encapsulated.

In some embodiments, the system 100 can be configured to be run automatically, manually and/or semi-automatically to process and quantitatively analyze samples to be used for gene delivery. In some embodiments, the system 100 can be used in conjunction with operative personnel and/or apparatus for performing analysis of samples containing GD particles using a suitable separation technique (e.g., capillary isoelectric focusing) followed by immobilization and immunoassay such that there is streamlined, semi-automatic, separation, labeling, visualization, detection, and/or quantification of a proportions of functional GD particles in samples with heterogenous mixtures of GD particles. In some embodiments, the system 100 can be configured to receive samples, read one or more identifiers (e.g., barcodes)

associated with the samples, identify information associated with the sample (e.g., the type of GD particles that are expected to be included (if any) in a sample) and based on the information chose binders, labels, and/or detection agents to quantitatively analyze the samples to determine an NA content and/or a protein content included in the samples. In some embodiments, the system 100 can be configured to store data and/or have access to a repository with stored data indicating a relationship between NA content and/or protein content in samples including a type of GD particles and known proportions of GD particles in a full, partial, and/or empty state. The system 100 can receive a test sample, read one or more identifiers (e.g., barcodes) associated with the test sample, identify information associated with the test sample (e.g., the type of GD particles that are expected to be included (if any) in the test sample) and based on the information (i) quantitatively analyze the test sample, and/or (ii) chose a stored relationship to apply the results of quantitative analysis of the test sample to determine a proportion of GD particles in the test sample in a full, partial, and/or empty state.

Figure 2:
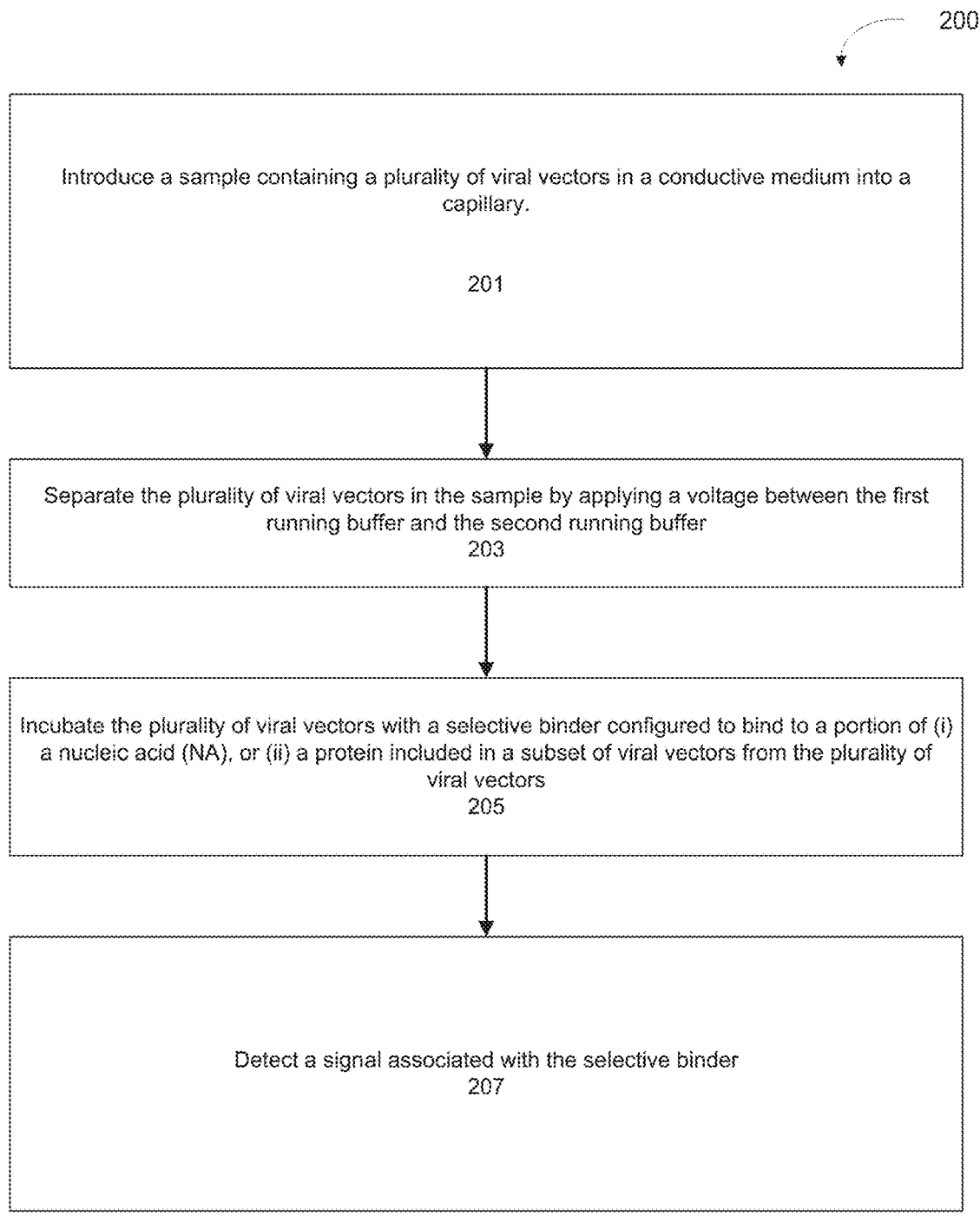
FIG. 2 is a flowchart of a method to analyze a sample containing a heterogenous mixture of particles for gene delivery, according to an embodiment.

FIG. 2 is a flow chart of a method 200 of analyzing a sample containing a mixture of GD particles, according to an embodiment. In particular, signals quantifying the amount of NA and/or protein associated with constituent GD particles focused at various isoelectric points can be determined. Based on features of the signals, a proportion of GD particles that are in a full, partial, and/or empty state can be determined and used to ascertain a quality of the sample to be used for gene delivery in a subject. The method 200 can be implemented by a system similar to the sample analysis system 100 described previously.

At 201, the method includes introducing a sample containing a plurality of viral vectors (GD particles) in a conductive medium into a capillary. In some implementations, the introducing the sample into a capillary can be such that a first end of the capillary is ionically coupled to a first running buffer having a first pH and a second end of the capillary is ionically coupled to a second running buffer having a second pH such that a pH gradient is formed along the capillary. The sample can be a crude sample, a sample in-process of manufacturing GD particles for gene delivery, obtained from cell lysates, or a purified sample of GD particles with known statuses or know proportions in full/empty status (e.g., standard samples). Preparing the sample can optionally include transfection, (ultra)centrifugation of the sample, size exclusion chromatography, (ultra)filtration, or any other suitable means of obtaining a sample containing a populations of GD particles. The first running buffer can be an acid held in a first running buffer reservoir for example in a cartridge associated with a sample holder of a sample analysis system that is substantially similar in structure and/or function to the sample holder 102 of system 100 described above. The second running buffer can be a base held in a second running buffer reservoir for example in a cartridge or a well associated with a sample holder of a sample analysis system that is substantially similar in structure and/or function to the sample holder 102 of system 100 described above.

At 203, the method 200 includes separating the plurality of viral vectors in the sample by applying a voltage between the first running buffer and the second running buffer. In some implementations, the separation of the analytes in the sample including the GD particles, can be based on their respective isoelectric points (pI). In some embodiments, the isoelectric points of the GD particles may be based on surface marker proteins (e.g., capsid proteins) on the GD particles. In some instances, the one or more methods used to isolate contents of grouped GD particles can include physically separating the contents of the sample such that impurities (e.g., "loose" or "free" NA that is not disposed in a viral vector) get washed away. In some implementations, the GD particles may be further separated based on one or more properties of the GD particles such as size, isoelectric point, polarity or charge carried by proteins, etc.

In some implementations, the method 200 can include an optional step (not shown in FIG. 2) including the immobilization of the separated GD particles along the fluid path defined by the lumen of the capillary. Immobilization can be carried out using any suitable method or technique. For example, in some implementations, a reactive moiety on the walls of the capillary can be activated to covalently immobilize the resolved analytes including GD particles in the fluid path. The reactive moiety can comprise any reactive group that is capable of forming any suitable linkage (e.g., linkage via ionic bonds, covalent bonds, hydrogen bonds, weak Van der Waal's forces, reversible bonds, and/or the like) to a group associated with one or more GD particles in the sample. For example, a reactive moiety can include a reactive group that is capable of forming covalent linkage with a corresponding reactive group of individual molecules of one or more GD particles in the sample. Thus, the reactive moiety can comprise any reactive group known in the art, so long as it is compatible with the methods and devices described herein. In some embodiments, the reactive moiety comprises a reactive group that is capable of forming a covalent linkage with a corresponding reactive group of an analyte of interest. In embodiments employing two or more reactive moieties, each reactive moiety can be the same, or some or all of the reactive moieties may differ. U.S. Pat. No. 7,935,489 entitled, "METHODS AND DEVICES FOR ANALYTE DETECTION," the disclosure of which is incorporated herein by reference in its entirety, describes some suitable methods that can be used to immobilize contents of a capillary. The separated, isolated, and/or immobilized GD particles and/or their contents (e.g., NA content, protein content) can be probed in any suitable manner to extract information about the presence and/or quantitative amount of protein content, genetic content, and/or other relevant information At 205, the method includes incubating, after separating, the plurality of viral vectors with a selective binder configured to bind to (i) a portion of a nucleic acid (NA), or (ii) a protein that may be included in a subset of viral vectors from the plurality of viral vectors. In some instances, NA can be probed to interact with known detection binders such that a successful binding can indicate the presence of any NA or genetic material (or in some instances specific NA sequences) which may in turn indicate properties of the GD particles, such as a full, partial, or empty status. For example, the selective binder can be configured to selectively bind to NA content (e.g., plasmid DNA) in the subset of viral vectors. In some instances, one or more specified proteins can be probed to interact with known detection binders such that a successful binding can indicate the presence of specific protein markers. For example, the selective binder can be configured to selectively bind to protein content (e.g., surface proteins such as proteins VP1, VP2, VP3 that occur on capsids of AAV vectors) associated with the subset of viral vectors.

In some implementations, the incubation with binders selective for NA content and the incubation with binders selective for protein content can be carried out in parallel using two separate capillaries separating and analyzing samples from the same source. In some implementations, the incubation with binders selective for NA content and the incubation with binders selective for protein content can be carried out in sequential order using two separate capillaries separating and analyzing samples from the same source.

At 207, the method includes detecting a signal associated with the selective binder. The detection of the signal can be performed using a sample prober as described herein. The obtained signal can be used to determine NA content or protein content based on the selectivity of the binder (e.g., determine NA content based on signals obtained using binders selective for NA, or determine protein content based on signals obtained using binders selective for proteins). In some implementations, the signals can be used to determine a quantity of the NA content or a quantity of the protein content included in the subset of viral vectors from the plurality of viral vectors to which the selective binder is bound. In some implementations, the signals can be used to determine an isoelectric point (pI) associated with the subset of viral vectors from the plurality of viral vectors that include the NA or the protein to which the selective binder is bound. The signals can be suitably analyzed to provide information or features (e.g., a peak intensity and/or an area under the curve of the signal emitted by components localized at a specified range of isoelectric points along the pH gradient in a capillary) related to the GD particles in the sample. In some instances, the probing can include one or more suitable forms of stimulating the grouped GD particles and/or the contents of the sample, using a stimulus that can elicit a corresponding response indicative of specific characteristics.

In some instances, the probing can include one or more methods of disrupting the capsid of the captured GD particles and/or disrupting the NA content/protein content associated with the GD particles to further probe with suitable detection binders. For example, the captured GD particles can be treated with a nuclease to disrupt NA content and then probed for signals associated with binder selective for NA content. Signals obtained after treatment with nuclease can be compared against signals obtained without the treatment of nuclease to ascertain that the signals associated with binders selective for NA content are originating from NA content withing GD particles (e.g., signals associated with or indicating NA content are expected to be diminished or extinguished after treatment with nucleases). In some implementations, signals associated with NA content ca n be compared with signals associated with protein content (before and after treatment with nucleases) for further confirmation of origin of signals (e.g., signals associated with or indicating protein content are not expected to be diminished or extinguished after treatment with nucleases).

Figure 3:
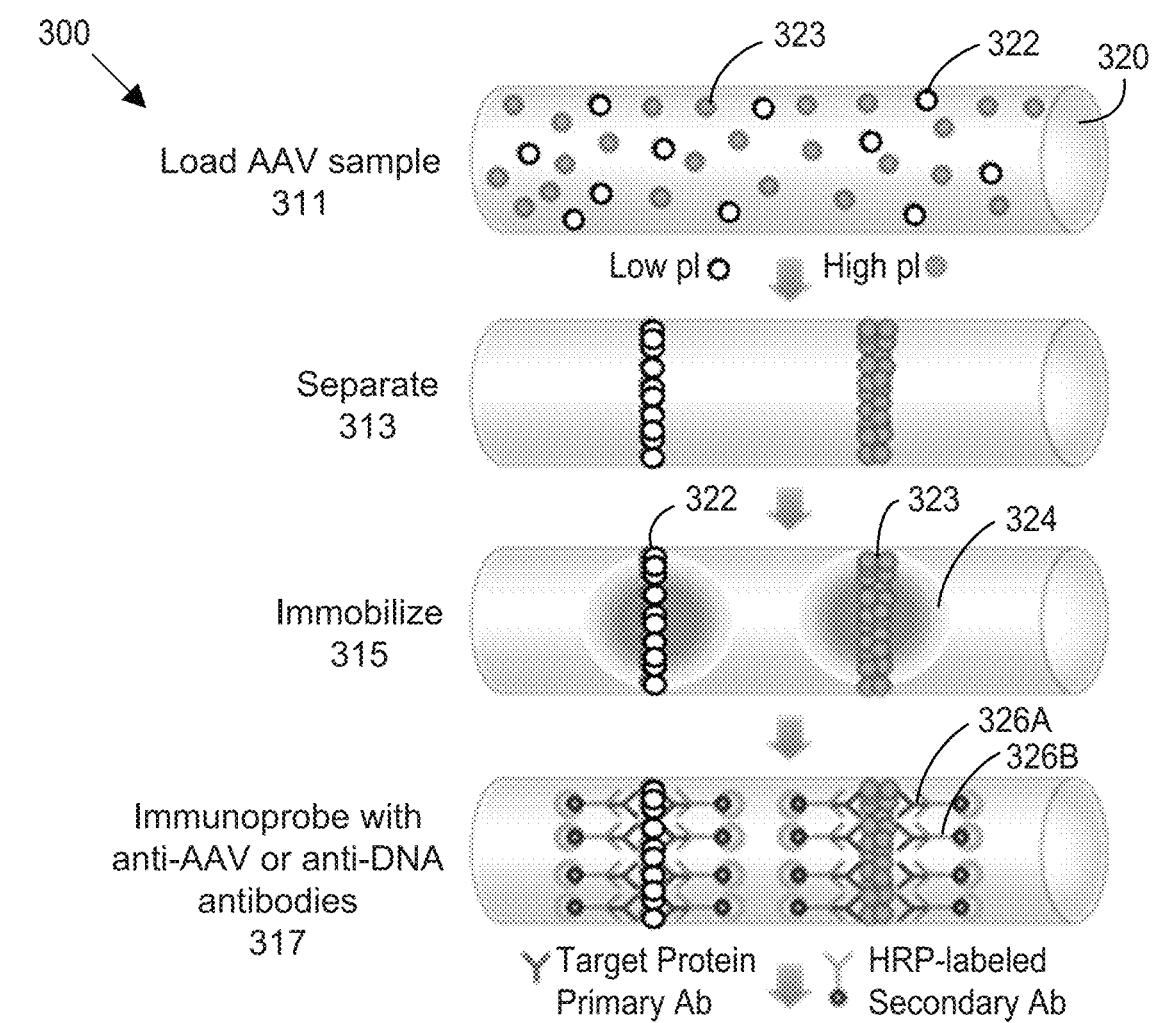
FIG. 3 is a schematic representation of a method to perform a quantitative analysis of a sample containing a mixture of particles configured for gene delivery, according to an embodiment.
Figure 3:
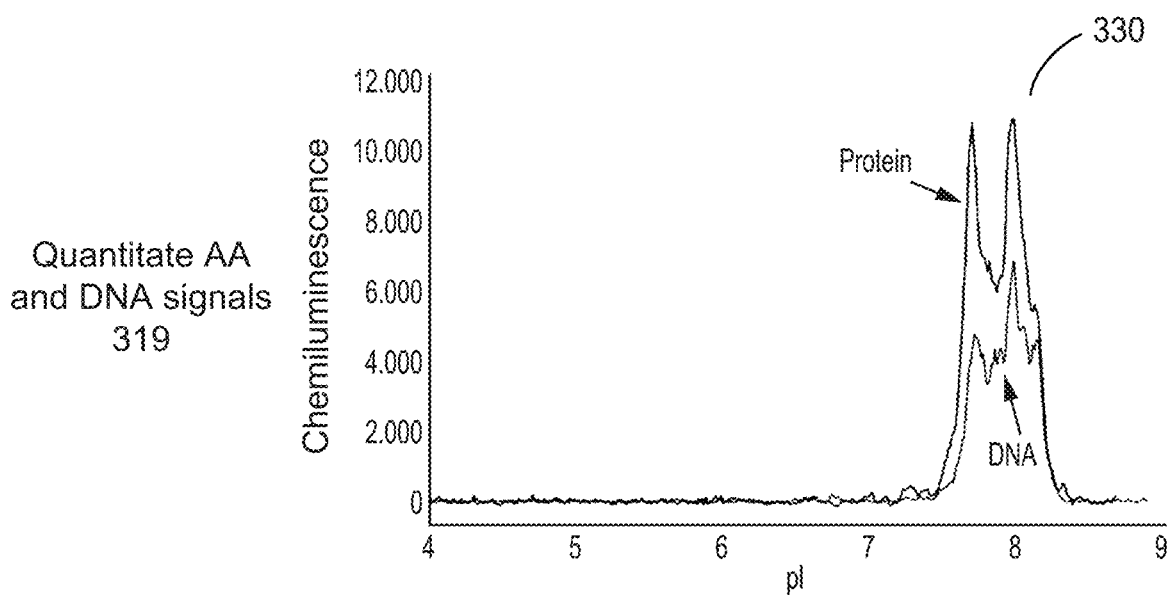

FIG. 3 shows a schematic representation of a method 300 of quantitatively analyzing a sample containing a heterogenous population of GD particles, according to an embodiment. Some or all events in method 300 can be substantially similar to or the same as events described in method 200 shown in FIG. 2. For example, the method 300 can be used to prepare and perform a quantitative analysis of a sample containing a mixture of GD particles in various states between full, partial, and/or empty with respect to the amount of NA content within the GD particles, and their implications for functional suitability or quality of the sample for gene delivery purposes. The method 300 can be implemented using a system substantially similar to the system 100 described herein. The method 300 includes, at 311, loading a sample containing a mixture of GD particles 322 and 323 onto a capillary 320. As described previously, the sample can be prepared in a conductive medium and loaded into one or more capillaries, through suction, electrokinetic injection, or any other suitable method. In the example in FIG. 3 the GD particles 322 can have a low isoelectric point (low pI) and the GD particles 323 can have a higher isoelectric point (high pI).

At 313, the method includes separating the analytes in the sample including the GD particles 322 and 323, and potentially removing impurities or other particles that may not be of interest, using a suitable separation technique such as isoelectric focusing. Isoelectric focusing can result in focusing and isolating groups of GD particles 322 and 323 based on their respective isoelectric points as shown in FIG. 3. As an example, since different AAV particles can have specific surface charge reflected in their isoelectric point (pI), only signals at a specific pI or a specific range of pI can be used to determine the NA and protein concentrations or content of the AAV particles of interest. The above described process segregates and/or removes impurities that have pIs that differ significantly from the GD particles of interests. For example, free nucleic acid typically has a very low pI and will be focused far away from GD particles 322 and 323 or flushed from the capillary during the focusing process. Other moieties that are not of interest (e.g., components other than GD particles 322 and 323) may similarly be distinguished from GDs of interest based on their isoelectric points.

At 315 the method 300 includes immobilizing the separated and isolated groups of analytes including the separated GD particles 322 and 323. Immobilization can be performed using any suitable method as desired such that the separated analytes including the GD particles can be fixed at a location along the fluid path in the lumen of the capillary. One or more analytes that are resolved in the fluid path can be immobilized such that detection agents or detection binders can be conveyed through the fluid path, to cause the detection agents or binders to selectively bind to or interact with the analytes (e.g., NA content, and/or protein content associated with the GD particles) and permit detection of the immobilized analytes including GD particles in the fluid path. As described herein, immobilizing can refer to substantially reducing or eliminating the motion of molecules in the fluid path. The immobilization can be via covalent bonds or non-covalent means such as via hydrophobic or ionic interaction.

In some embodiments, the fluid path can include one or more reactive moieties that can interact and/or capture molecules or particles in the sample. Such a reactive moiety can be used to covalently immobilize the resolved analyte or analytes in the fluid path. The reactive moiety can comprise any reactive group that is capable of forming a covalent linkage with a corresponding reactive group of individual molecules of the sample. Thus, the reactive moiety can comprise any reactive group known in the art, so long as it is compatible with the methods and devices described herein. The reactive moiety can be attached directly, or indirectly to the fluid path. In some embodiments, the reactive moiety can be supplied in solution or suspension, and the reactive moiety may form bridges between the wall of the fluid path and the molecules in the sample upon activation. The reactive moiety can line the fluid path or, in another embodiment, may be present on a linear or cross-linked polymer in the fluid path. The polymer may or may not be linked to the wall of the fluid path before and/or after activation. In some embodiments, photoimmobilization in the fluid path can be accomplished by the activation of one or more photoreactive groups. A photoreactive group comprises one or more latent photoreactive groups that upon activation by an external energy source, such as a UV light, forms a covalent bond with other molecules. See, for example, U.S. Pat. Nos. 5,002,582 and 6,254,634, 7,935,479, and 7,846,676, the disclosures of which are incorporated herein by reference. In addition to the use of photo-activatable chemistry described above, chemical or thermal activation may also be employed. In some embodiments, the reactive moiety comprises a functional group that can be used to attach the reactive moiety to an analyte by forming a covalent linkage with a complementary group present on the analyte. Pairs of complementary groups capable of forming covalent linkages are well known in the art. In some embodiments, the analyte comprises a nucleophilic group and the reactive group comprises an electrophilic group. In other embodiments, the reactive group comprises a nucleophilic group and the analyte comprises an electrophilic group. Complementary nucleophilic and electrophilic groups, or precursors thereof that can be suitably activated, useful for forming covalent linkages stable in assay conditions are well known and can be used. Examples of suitable complementary nucleophilic and electrophilic groups, as well as the resultant linkages formed there from, are provided in U.S. Pat. No. 6,348,596, the entire disclosure of which is hereby incorporated by reference.

Returning to the method 300 in FIG. 3, in some implementations, the method can include an optional step, not shown in FIG. 3, of rendering the NA content within the GD particles more accessible to the immunoprobes or binders configured to bind to NA content (e.g., anti-DNA antibodies or markers specific for certain NA segments, etc.). The increase in accessibility to immunoprobes configured to selectively bind to NA content can be, for example, generating access points in the GD particles (e.g., capsids) or by suitably opening the particles such that the binders can enter into the GD particles to interact with the NA content while the GD particles remain intact with the NA content remaining within the GD particles (and remaining focused at the pI associated with the GD particles). In some implementations, there may not be an explicit step of rendering the GD particles more open as the procedures followed in separation and/or immobilization of the GD particles may render the GD particles open to allow the NA specific binders to enter into the GD particles and interact with the NA content.

At 317, the method includes probing the separated and immobilized GD particles 322 and 323 with immunoprobes including detection binders 326A and 326B that target specific NA content (e.g., anti-DNA antibodies) and/or detection binders targeting specific protein content (e.g., anti-AAV antibodies) associated with the GD particles. A detection agent or binder can be capable of binding to or interacting with an analyte (e.g., NA or protein) to be detected. Contacting the detection agent or binder with the analyte or analytes of interest can be by any method known in the art, so long as it is compatible with the methods and devices described herein. Examples for conveying detection agents through the fluid path include, but are not limited to, hydrodymic flow, electroendosmotic flow, or electrophoresis.

In some embodiments, the detection agents or binders can include one or more label moiety(ies). In embodiments employing two or more label moieties, each label moiety can be the same, or some, or all, of the label moieties may differ. In some embodiments, the label moiety can include a chemiluminescent label that can comprise any entity that provides a light signal and that can be used in accordance with the methods and devices described herein. A wide variety of such chemiluminescent labels are known in the art. See, for example, U.S. Pat. Nos. 6,689,576, 6,395,503, 6,087,188, 6,287,767, 6,165,800, and 6,126,870 the disclosures of which are incorporated herein by reference. Some example labels include enzymes capable of reacting with a chemiluminescent substrate in such a way that photon emission by chemiluminescence is induced through enzymatic activity. Such enzymes may include peroxidase, beta-galactosidase, phosphatase, or others for which a chemiluminescent substrate is available. In some embodiments, the chemiluminescent label can be selected from any of a variety of classes of luminol label, an isoluminol label, etc. In some embodiments, the detection agents or binders comprise chemiluminescent labeled antibodies. In some embodiments, the detection agents comprise chemiluminescent substrates. Depending on their charge, the chemiluminescent substrates can be supplied from either end of the fluid path, once the analyte is immobilized in the fluid path. Uncharged substrates can be supplied from either end of the fluid path by hydrodynamic flow or electroendosmotic flow, for example. Example chemiluminescent substrates include Galacton substrate. In some embodiments, the label moiety can comprise a bioluminescent compound. Bioluminescence is a type of chemiluminescence found in biological systems in which a catalytic protein increases the efficiency of the chemiluminescent reaction. The presence of a bioluminescent compound is determined by detecting the presence of luminescence. Suitable bioluminescent compounds include, but are not limited to luciferin, luciferase and aequorin. In some embodiments, the label moiety comprises a fluorescent dye. The fluorescent dye can comprise any entity that provides a fluorescent signal and that can be used in accordance with the methods and devices described herein. A fluorescent dye can include a resonance-delocalized system or aromatic ring system that absorbs light at a first wavelength and emits fluorescent light at a second wavelength in response to the absorption event. For example, fluorescent dyes can be selected from any of a variety of classes of fluorescent compounds, non-limiting examples include xanthenes, rhodamines, fluoresceins, cyanines, phthalocyanines, squaraines, bodipy dyes, coumarins, oxazines, and carbopyronines. In some embodiments, for example, where detection agents contain fluorophores, such as fluorescent dyes, their fluorescence is detected by exciting them with an appropriate light source, and monitoring their fluorescence by a detector sensitive to their characteristic fluorescence emission wavelength. In some embodiments, the detection agents comprise fluorescent dye labeled antibodies.

In embodiments, using two or more different detection agents, which bind to or interact with different analytes, different types of analytes can be detected simultaneously. In some embodiments, two or more different detection agents, which bind to or interact with the one analyte, can be detected simultaneously. In some embodiments, using two or more different detection agents, one detection agent, for example a primary antibody, can bind to or interact with one or more analytes to form a detection agent-analyte complex, and second detection agent, for example a secondary antibody (including a label), can be used to bind to or interact with the detection agent-analyte complex.

In some embodiments, two different detection agents, for example antibodies for NA and antibodies for protein content associated with GD particles or antibodies configured to selectively bind to two or more different NA and/or protein segments of interest can enable detection of both the NA and the protein content of interest or the two or more different NA and/or protein segments of interest. For example, the different chemiluminescent substrates used would be selected such that they emit photons of differing color. Selective detection of different colors, as accomplished by using a diffraction grating, prism, series of colored filters, or other means allow determination of which color photons are being emitted at any position along the fluid path, and therefore determination of which detection agents are present at each emitting location. In some embodiments, different chemiluminescent reagents can be supplied sequentially, allowing different bound detection agents to be detected sequentially.

Signals emitted by the detection agents or binders can be detected via a detector. At 319, the method includes quantitating the signals 330 obtained that may be associated with NA content and/or protein content and based on the signals determining an amount of NA content and/or protein content. In some implementations, the quantitation can include determining an isoelectric point or a range of isoelectric points that may be associated with a group of GD particles.

In some implementations, the quantification can include calculating one or more statistics associated with a signal. For example, quantification can include determining a peak of a signal and an isoelectric point associated with the peak. As another example, quantification can include determining an area under the curve (AUC) of the signal within a specified range of isoelectric points.

In some implementations, the method can include comparing the signal associated with NA content of a group of GD particles and the signal associated with protein content of the group of GD particles, and based on the comparison determine a quantity of NA content and/or a proportion of GD particles in a full/empty/partial state. As an example, samples containing similar number of concentrations of GD particles, for example AAV particles, but with varying proportion of GD particles in a full state (i.e., including plasmid NA content) can result in comparable signals associated with protein content but with dissimilar signals associated with NA content. Thus, comparing the signals associated with the protein content and the signals associated with the NA content of two or more samples can help determine relative proportions of GD particles in full state. FIGS. 4A-4D schematically illustrate an example implementation of such a comparison of signals.

Figure 4A:
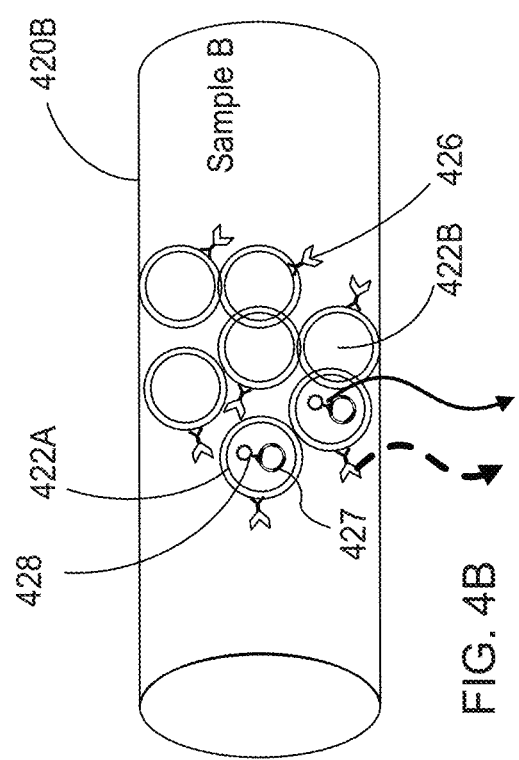
FIGS. 4A and 4B are schematic representations of capillaries used to analyze samples including mixtures of particles for gene delivery, according to an embodiment.
Figure 4B:
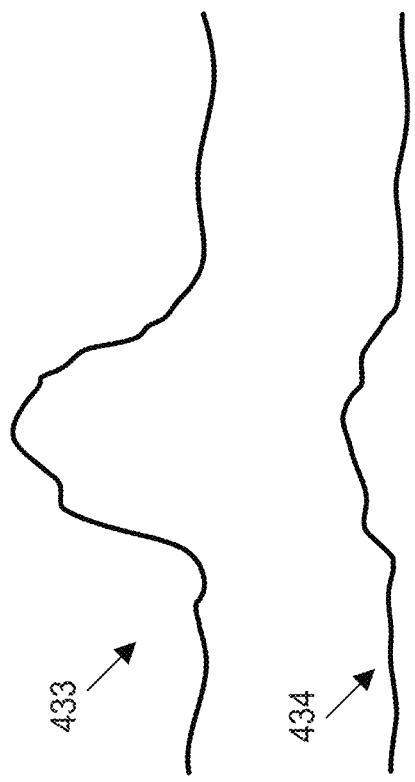
Figure 4C:
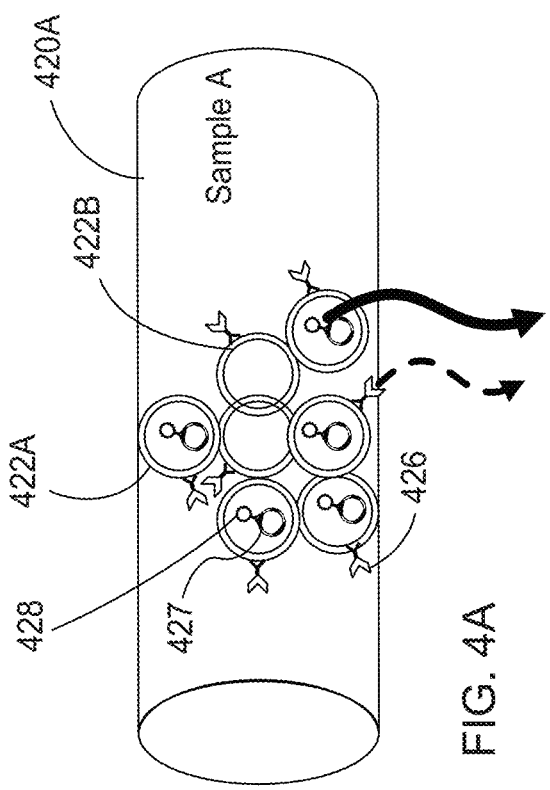
FIGS. 4C and 4D are schematic representations of signals obtained from capillaries used to analyze samples having particles used for gene delivery, according to an embodiment.
Figure 4D:
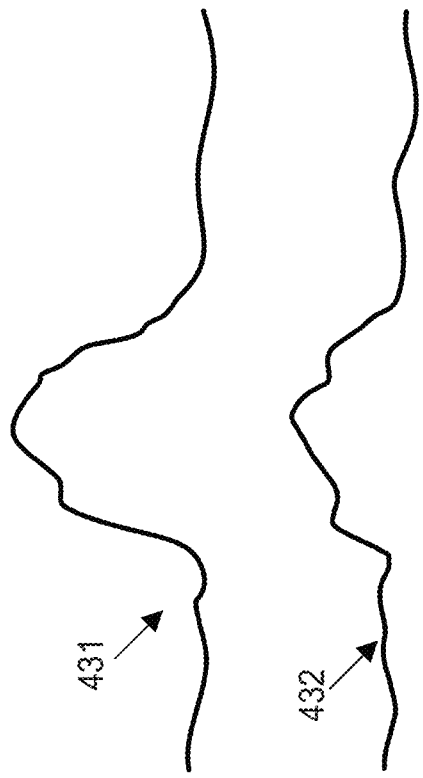

FIGS. 4A and 4B show two capillaries 420A and 420B, respectively, carrying two samples A and B that have undergone separation and focusing. In the illustrated example, samples A and B can include GD particles of the same type. Sample A, however, can include a greater proportion of the GD particles in a full state 422A, that is including NA content 427 (e.g., plasmid DNA), and a lesser proportion of the GD particles in an empty state 422B, that is lacking the NA content 427 (e.g., plasmid DNA). Using the systems (e.g., system 100) and/or methods (e.g., methods 200 and/or 300) described herein, the GD particles can be assayed with immunoprobes configured to selectively bind to the protein content and/or the NA content associated with the GD particles. For example, protein specific detection agents or binders 426 (e.g., antibodies configured to selectively bind to capsid proteins know to occur in capsids of AAV particles used as GD particles) can be used to selectively bind to and label the protein content associated with the GD particles 422A and 422B. NA specific detection agents or binders 428 (e.g., anti-DNA antibodies configured to selectively bind to plasmid DNA within the capsids of AAV particles that may be in a full state) can be used to selectively bind to and label the NA content associated with the GD particles 422A. The protein specific detections agents and the NA specific detections agents can be configured to be probed (e.g., stimulated using light, heat, chemical, and/or the like) to emit signals (e.g., chemiluminescence, native fluorescence, acquired fluorescence, absorbance, and/or the like) indicating their presence and/or concentration, and thereby the presence and/or concentration of the associated analytes to which the detection agents are bound. FIGS. 4C and 4D illustrate example signals that can be obtained from the GD particles in response to probing. The signals 431 and 433 can be associated with protein specific detections agents associated with sample A and sample B, respectively. The signals 432 and 434 can be associated with NA specific detections agents associated with sample A and sample B, respectively. As shown, in some implementations, one or more statistics obtained from the signals 431 and 433 associated with protein specific detections agents can be comparable between the samples A and B. For example, a peak statistic or an AUC statistic obtained from signals 431 and 433 can be comparable. This can indicate a comparable amount or quantity of protein content in the samples A and B tested. The one or more statistics obtained from the signals 432 and 434 associated with NA specific detections agents, however, can be different between the samples A and B. Such a difference can arise from the different number of GD particles in the full state, that is including the plasmid DNA 427, and therefore a different amount of NA specific detection agents 428 bound to the NA content and in turn emitting a signal 432, 434. For example, a peak statistic or an AUC statistic obtained from signals 432 and 434 can be distinctly different with a larger peak and/or AUC measured from signal 432 associated with the sample A than from signal 434 associated with sample B. This can indicate a varying amount or quantity of NA content in the samples A and B tested. A comparison between the signals 431 and 433 associated with protein content in the samples, and between the signals 432 and 434 associated with NA content in the samples can help ascertain the difference in proportion of GD particles in the full state (or empty state) in the samples A and B. In some implementations, the comparison samples can be performed with or without the signals 431, 433 associated with the protein content. However, signals 431 and 433 can be useful to account for variability in mass and/or volume of sample loaded in runs. Said in another way, in some embodiments, signals associated with protein content in samples with GD particles can be used to normalize the signals 432, 434 associated with NA content or to account for differences in amount of GD particles in each sample. In some embodiments, such a comparison between signals 432, 434 associated with NA content can be performed without any signals 431, 433 associated with protein content in the samples.

Figure 5A:
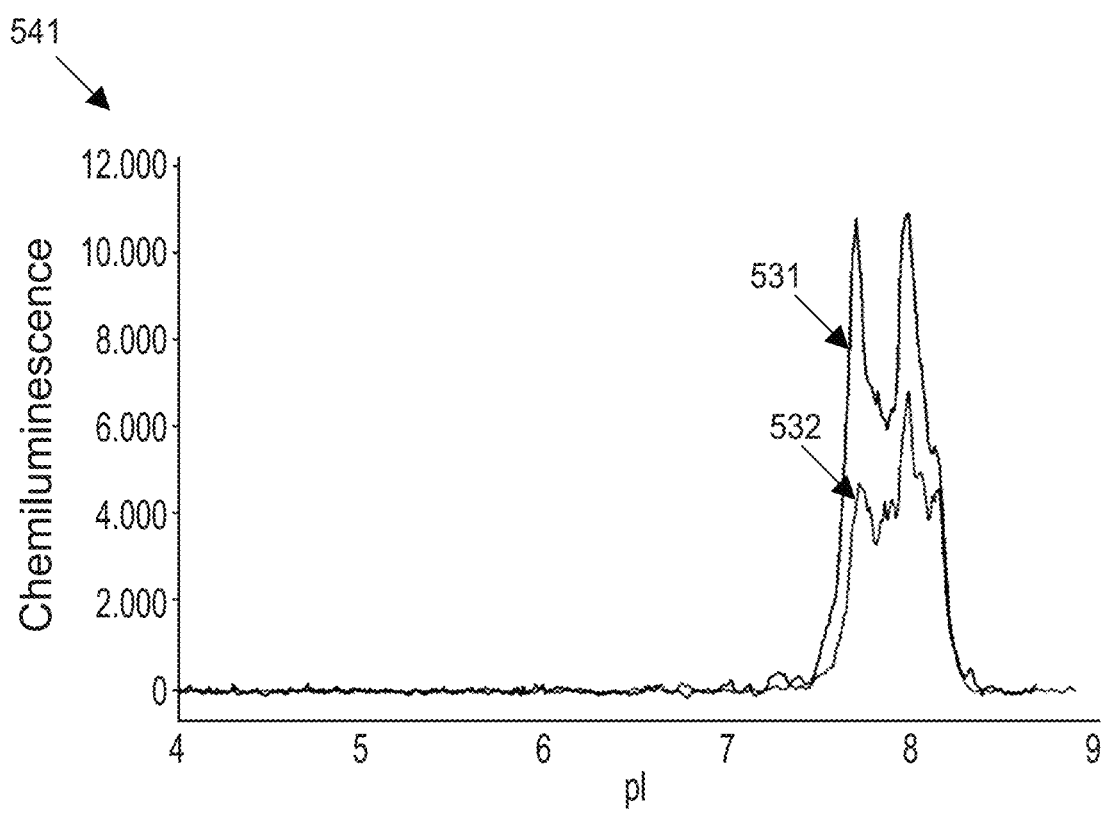
FIGS. 5A and 5B are graphs showing experimentally obtained traces representing signals associated with protein and NA content obtained from samples having particles for gene delivery, according to an embodiment.
Figure 5B:
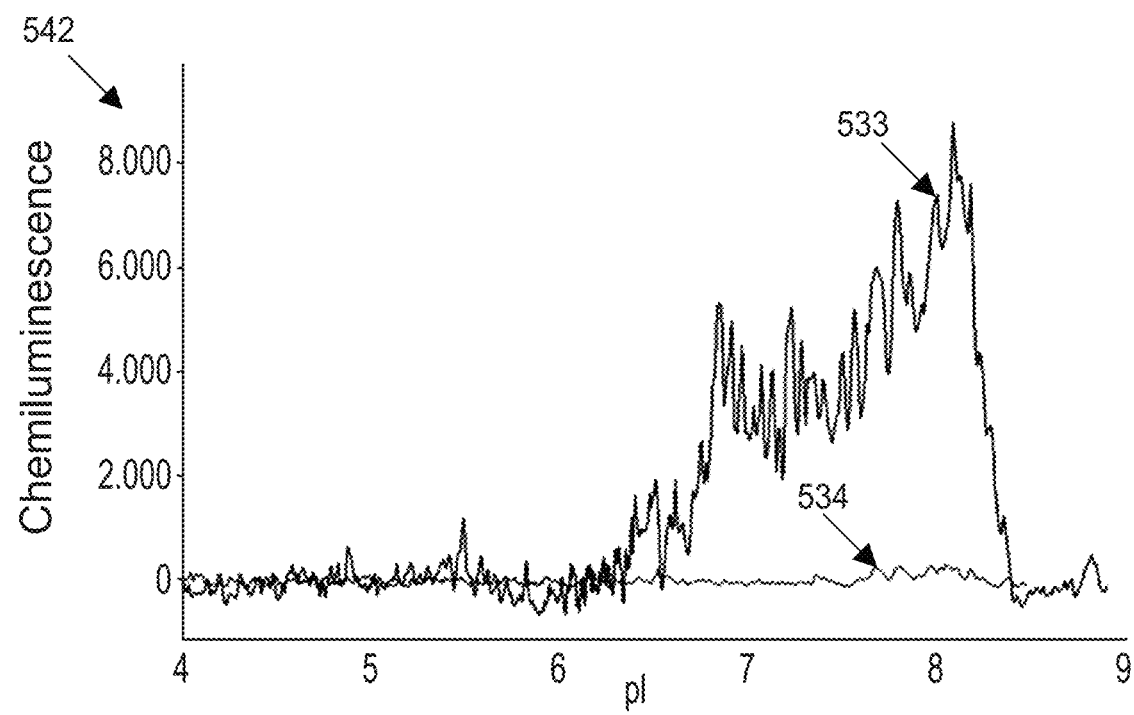

FIGS. 5A and 5B show example chemiluminescence signals obtained from analysis of two samples containing GD particles, using systems and/or methods described herein. Sources with AAV9 particles with varying proportions in full and empty state were used. A sample from a first source had 77% of the AAV9 particles in full state (23% in empty state) and a sample from the second source had 91% of the AAV9 particles in the empty state (9% in full state). The sources were purchased from a commercial supplier (Virovek) where the empty/full status was measured through a proprietary Qbit assay (www.virovek.com). These samples were separated on commercially available Peggy Sue instrument from ProteinSimple® configured to perform IEF before interrogation with anti-AAV protein antibodies and anti-DNA antibodies. The resulting chemiluminescent signals 531, 532, 533, and 534 were detected and plotted against the pH gradient in the capillaries indicating range of isoelectric points.

The signals 531, 532 and the signals 533, 534 in FIGS. 5A and 5B can be similar to the illustrative signals 431, 432 and the signals 433, 434, respectively, described above. FIG. 5A shows plot 541 that includes chemiluminescence intensity signals 531 and 532 plotted against a range of isoelectric points on the x-axis. The signal 531 is associated with protein content in AAV9 particles in a first sample obtained from the first source and focused using isoelectric focusing and the signal 532 is associated with NA content in the AAV9 particles from the first sample or from a second sample obtained from the same first source as the first sample. FIG. 5B shows plot 542 that includes chemiluminescence intensity signals 533 and 534 plotted against a range of isoelectric points on the x-axis. The signal 533 is associated with protein content in AAV9 particles in a third sample obtained from the second source different from the first source and focused using isoelectric focusing and the signal 534 is associated with NA content in the GD particles from the third sample or from a fourth sample obtained from the same second source as the third sample. Based on the comparison between signals 532 and 534 it can be determined that the sample from the second source includes lesser NA content as indicated by a smaller peak and/or smaller AUC statistic associated with signal 534 compared to signal 532. The determination of lesser NA content in source B can be used to determine that a lesser proportion of GD particles in the second source are in a full state compared to a greater proportion of GD particles in the first source that may be in full state. The signals 531 and 533 associated with protein content in the samples from the first source and the second source respectively, can be used to normalize against differences in mass or quantity of GD particles between the sources. Said in another way, signals 531 and 533 associated with protein content can be used to account for potential differences in amount of GD particles in samples obtained from the first source and the second source irrespective of their state. Signals 531 and 533 can also serve to indicate where strong NA signals should occur if GD particles are full. FIG. 5A, which does contain a strong NA signal 532, therefore represents GD particles with a significant full fraction. FIG. 5B, however, which shows a strong proteins signal 533 and a weak NA signal 534 indicates that the sample contains mostly empty GD particles. This finding is in confirmation and consistent with the data that the first source is known to have 77% GD particles in full state and the second source is known to have 9% GD particles in the full state.

In some implementations, the statistics, such as AUC, AUC within a pre-defined (pI) window, peak height (at or near an expected pI) can be obtained for signals associated with known and/or well characterized samples with known concentrations of GD particles in a particular state (e.g., full, partial, and/or empty state). Such signal statistics can be obtained from the NA signal alone, or normalized by a similar measurement of a protein signal (e.g., ratios of AUCs of protein and NA signals). The statistics associated with the standardized samples can be used to establish a relationship between the statistic and a proportion of GD particles that may be in a given state (e.g., full, partial, or empty). In some implementations, the relationship can then be used to predict a proportion of GD particles in a full, partial, or empty state in an unknown test sample containing comparable GD particles. In some implementations, the predicted proportion of GD particles in a specified state can be used to determine a suitability or quality of a sample to be used for gene delivery in therapy, research, etc.

Figure 6:
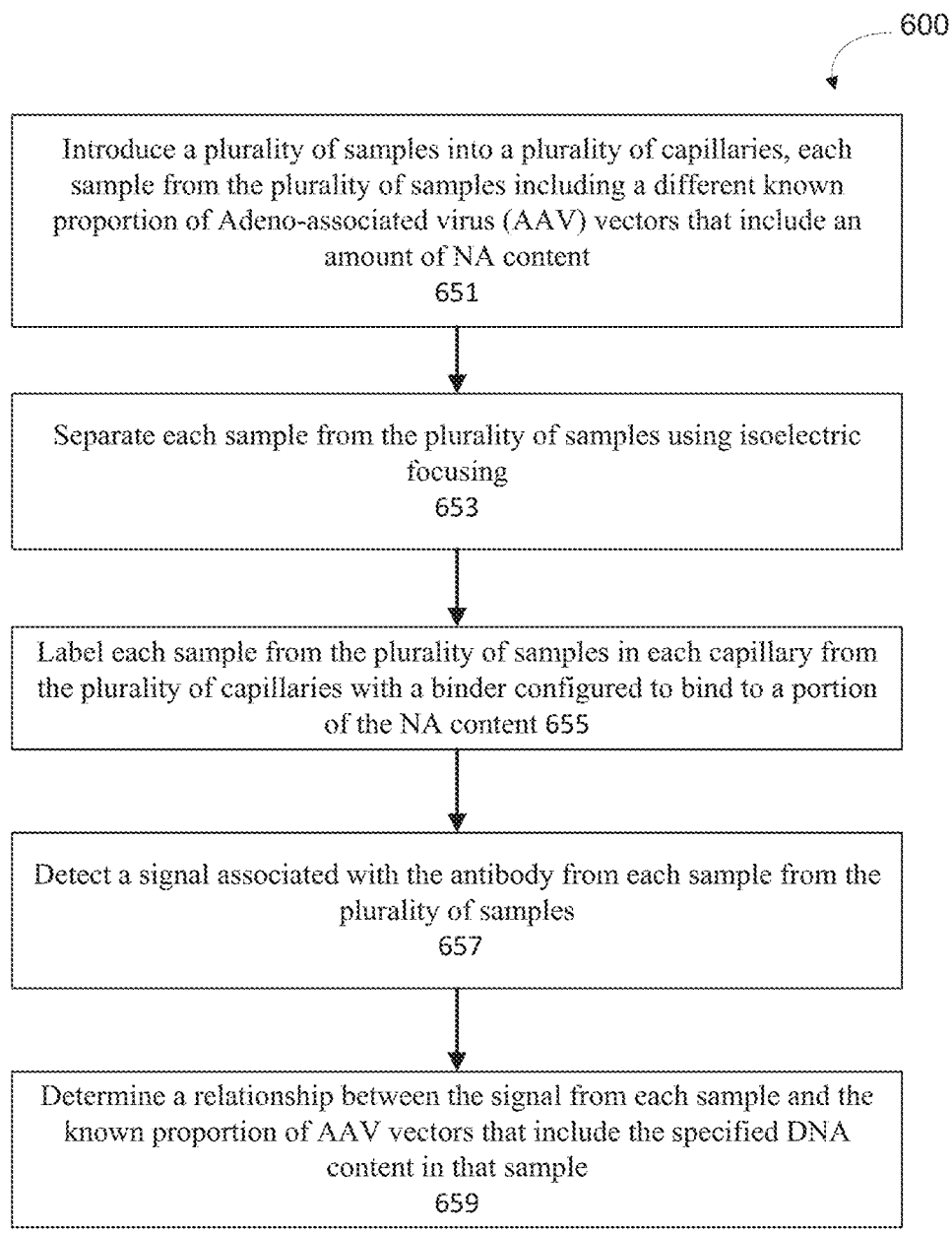
FIG. 6 is a flowchart of a method to analyze samples containing heterogenous mixtures of particles configured for gene delivery, according to an embodiment.

FIG. 6 shows a flow chart of a method 600 to analyze samples containing heterogenous mixtures of particles configured for gene delivery to establish a relationship between a signal statistic obtained from a sample and a proportion of GD particles that may be in a given state (e.g., full, partial, or empty) in that sample, according to an embodiment. The method 600 can be implemented using a system similar to the system 100 described above and/or using portions of methods described above including methods 200, and/or 300. The samples can be well characterized samples with GD particles of know state or know proportion of GD particles in a full, partial, and/or empty state. In some implementations, the well characterized samples can be prepared by mixing varying amounts of two samples with known proportions of GD particles in a full status. For example, well characterized samples with intermediate proportions of GD particles in full state can be prepared by mixing a first sample with a high known proportion (e.g., 77%) of GD particles in the full state and a second sample with a low known proportion (e.g., 9%) of GD particles in full state. The mixing can be done in varying amounts to generate a plurality of samples with intermediate proportions of GD particles in full state that gradually vary between the first sample and the second sample. For example, the intermediate samples can be prepared by mixing the first sample and the second sample in varying ratios, for example in ratios of 1:4, 1:2, 1:1, 3:1, 4:1, and 5:1. The plurality of samples including the first sample and the second sample can be used to establish a relationship between known quantities or proportions of GD particles in a given state (e.g., full state) and the signals associated with NA content and/or protein content obtained from analyzing the samples as described herein.

At 651 the method 600 includes introducing a plurality of samples into a plurality of capillaries, each sample from the plurality of samples including a different known proportion of Adeno-associated virus (AAV) vectors that include an amount of NA content.

At 653, the method includes separating each sample from the plurality of samples using isoelectric focusing. At 655, the method includes labeling each sample from the plurality of samples in each capillary from the plurality of capillaries with a binder configured to bind to a portion of the NA content. At 657, the method includes detecting a signal associated with the antibody from each sample from the plurality of samples.

At 659, the method includes determining a relationship between the signal from each sample and the known proportion of AAV vectors that include the specified DNA content in that sample. The signal from each sample can be used to extract features (e.g., peak intensity, isoelectric point, AUC, etc.). The features from each sample can be quantified and/or compared against the known proportion of Adeno-associated virus (AAV) vectors that include an amount of NA content (e.g., in a full state) in that sample. The comparison can be analyzed using any suitable method (e.g., regression analysis) to determine a function that optimally describes the relationship between the features quantified and the known proportion of AAV vectors in a given state. For example, the quantified feature and the corresponding known proportion of AAV vectors in a full state can be fit with a function using regression analysis (e.g., linear regression) to estimate a straight line function that best fits the points in a curve plotting the quantified feature against the known proportion of AAV vectors in full state.

The method 600 can be used to determine the relationship using a matrix of well characterized samples or controlled mixtures of well characterized samples containing GD particles, and then followed by analysis of one or more test samples with similar GD particles as the well characterized samples but with unknown mixtures of the GD particles in various states including full, partial, and/or empty. The relationship can then be used to predict proportions of GD particles in full state in unknown test samples. In some implementations, a matrix of well characterized samples and unknown test samples can be run at the same time. In some implementations, a system can rely on stored relationship functions derived from analysis of previously-measured well characterized samples to evaluate unknown test samples containing GD particles comparable to the GD particles in the previously-measured well characterized samples, and/or analyzed using binders comparable to those used to analyze the previously-measured well characterized samples.

In an example implementation, a plurality of well characterized samples were prepared by mixing varying ratios of a first sample (e.g., an enriched sample) of AAV9 particles known to have 77% of the AAV9 particles in a full state and a second sample (e.g., a depleted sample) of AAV9 particles known to have 9% of the AAV9 particles in a full state. The first sample and the second sample were purchased from commercial supplier (Virovek) with the know proportions quantified using an independent Qbit assay. The plurality of samples were prepared by mixing the enriched first sample and the depleted second sample in the following ratios: 1:4, 1:2, 1:1, 3:1, 4:1, and 5:1. The plurality of samples were separated and analyzed for the protein content and NA content by following methods 200, 300, and/or 600, as described above. The separated samples were interrogated with anti-AAV protein antibodies and anti-DNA antibodies tagged with suitable markers and the resulting chemiluminescence was detected and plotted as a function of range of isoelectric points in the pH gradient used for separation.

Figure 7A:
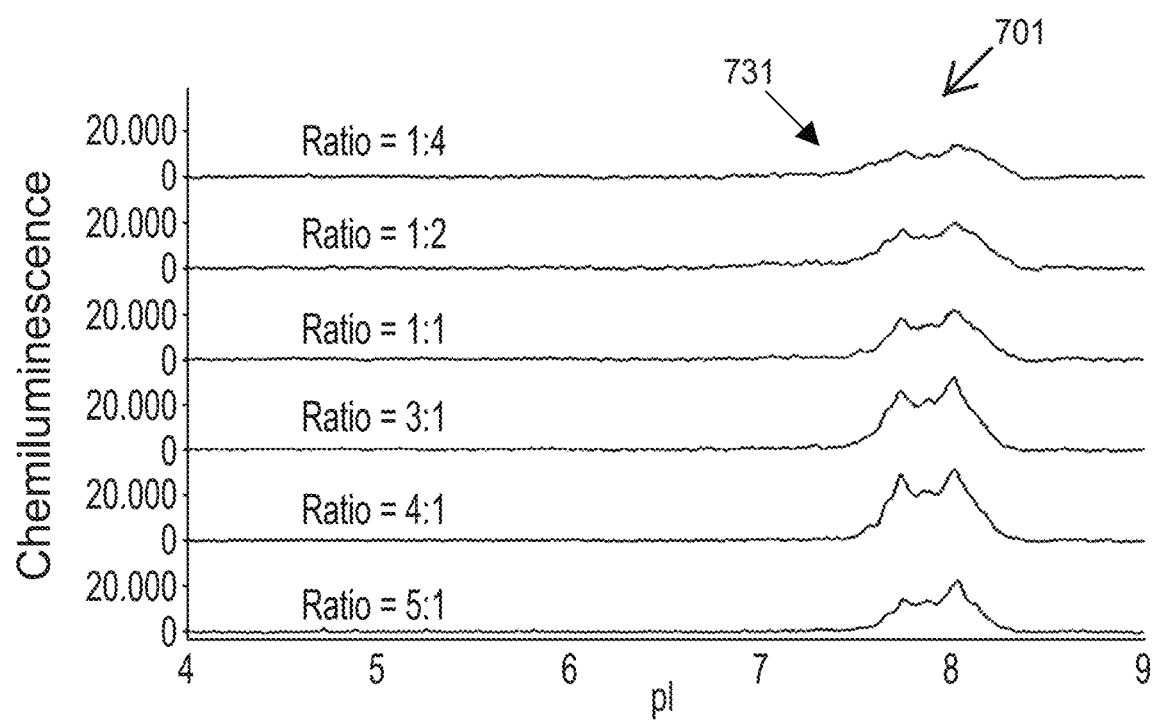
FIGS. 7A and 7B include graphs showing experimentally obtained traces representing signals associated with protein and NA content obtained from samples having particles for gene delivery.
Figure 7B:
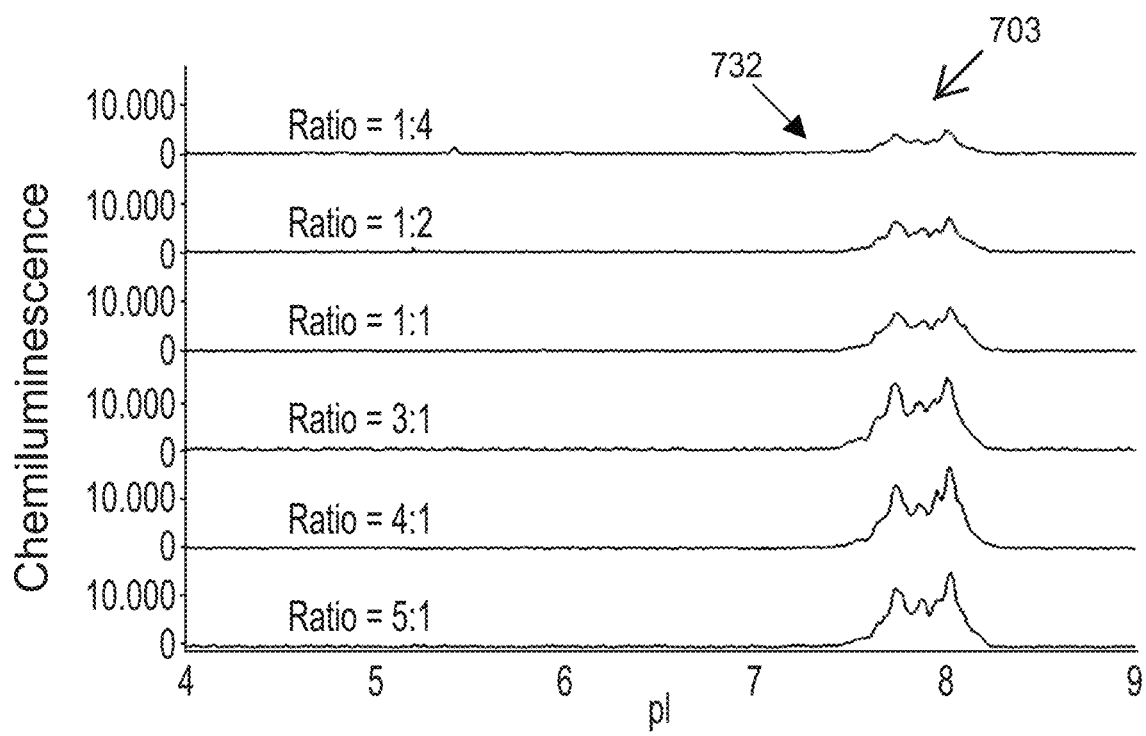
Figure 8A:
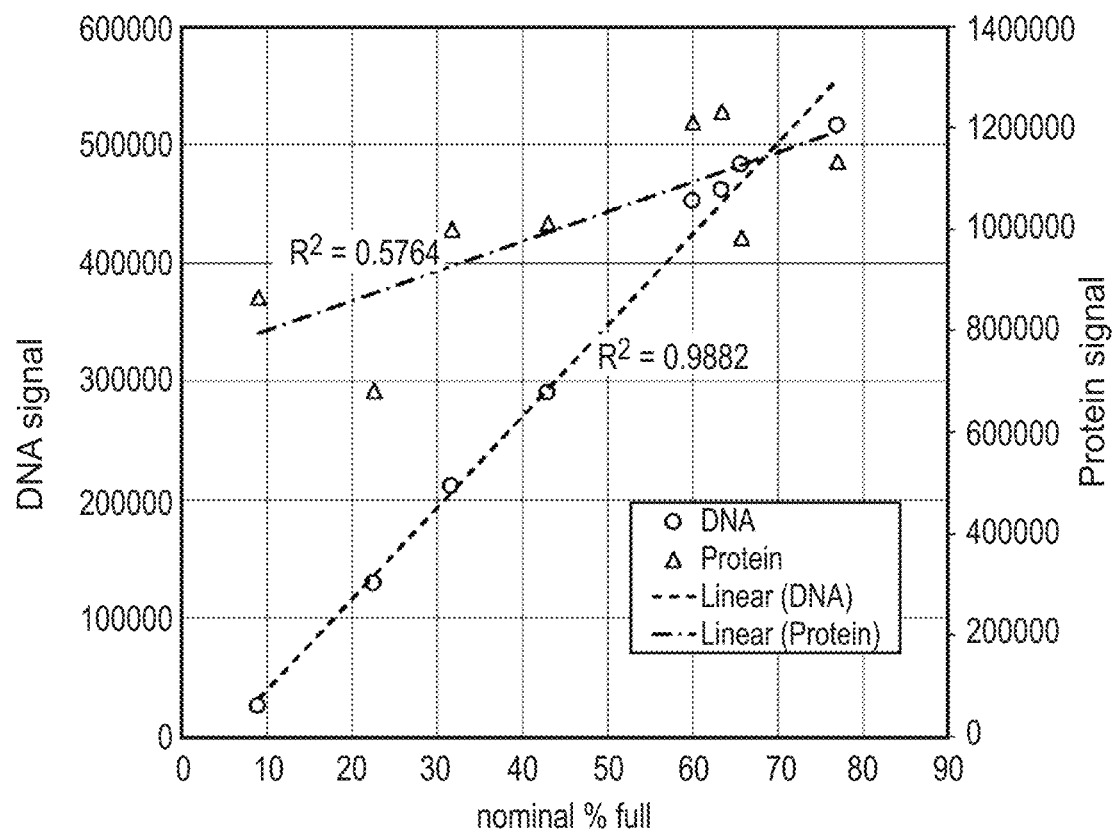
FIG. 8A is a graph showing a plot of an amount of signal associated with NA content as a function of a known proportion of particles having NA content in the samples, and an amount of signal associated with protein content as a function of a known proportion of particles having NA content in the samples.
Figure 8B:
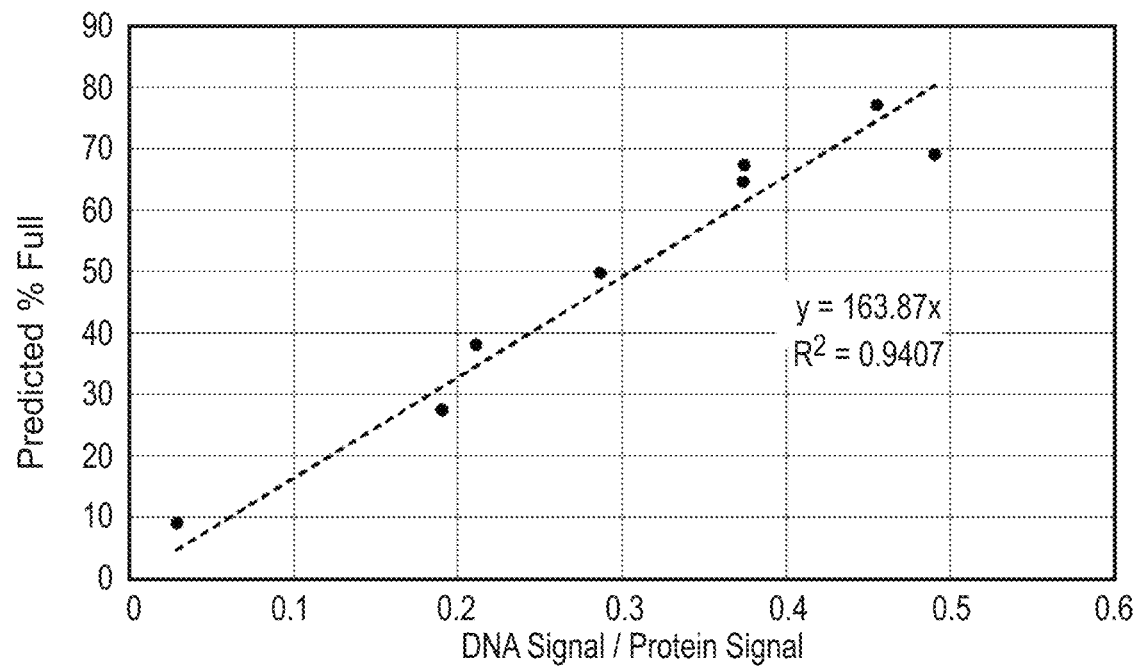
FIG. 8B is a graph showing an experimentally obtained relationship between data representing amounts of NA content, quantified in a set of samples having mixtures of particles for gene delivery, and a known proportion of particles having NA content in the samples.

FIG. 7A shows a plot 701 of signals 731 associated with protein content in the plurality of well characterized samples including varying proportions of AAV9 particles in a full state, plotted as a function of range of isoelectric points. FIG. 7B shows a plot 703 of signals 732 associated with NA content in the plurality of well characterized samples. FIG. 8A shows a plot of the AUC statistics of protein signals similar to 731 and NA signal similar to 732, generated by mixing the 77% full and 9% full samples in the following ratios 0:1, 1:4, 1:2, 1:1, 3:1, 4:1, 5:1, 1:0. The plot shows the quantification of NA content (left y-axis) and the quantification of protein content (right y-axis) in each sample against the nominal proportion of AAV9 particles in the full state in each sample indicated on the x-axis. Stated similarly, the nominal % full values on the x-axis are generated assuming equal concentrations of the 77% full and 9% full samples that were mixed together in the known ratios. In FIG. 8A, the positive slope of the linear fit of the protein signal indicates that the 77% full sample has a higher concentration of AAVs. The nominal % full values can then be corrected to actual % full values by noting that the linear fit of the protein signal predicts about 1.5 times more AAVs in the 77% full sample as compared to the 9% full sample (assuming that the increase in protein was caused by a higher concentration of AAVs). FIG. 8B shows a calibration curve created by dividing the DNA statistics by the protein statistics shown in FIG. 8A, after correcting the nominal % full values to actual % full. Alternately, a similar calibration curve can be generated using a plurality of AAV samples (preferably three or more) where the % full value has been determined by an independent method. The accuracy of the calibration may be improved by increasing the number of known samples and/or by running replicates of each known sample to reduce the impact of measurement variation. The calibration curve can be applied to measure unknown samples to determine a proportion of AAV particles in the full status. Similarly stated, the relationship shown in FIGS. 8A and 8B can be used to predict a proportion of AAV particles in a test sample with similar AAV particles but of unknown concentration and an unknown state or unknown proportion in a full state. The test sample can be separated, interrogated, and analyzed following a procedure similar to that used for the well characterized samples as described herein. The signals associated with NA content and protein content in the test sample can be quantified to calculate AUCs as done for the well characterized samples. The DNA AUC can be divided by the protein AUC, and that ratio can be looked up on the curve (line) shown in FIG. 8B. The resulting ratio can be located along the straight-line curve shown in FIG. 8B and projected onto the y-axis to obtain a corresponding percentage value which can predict a proportion of AAV particles in the test sample that may be in the full state. It should be understood that in other implementations the DNA statistic shown in FIG. 8A can be used to predict a proportion of AAV particles in a test sample, for example, for samples for which it is known or expected that protein content is substantially constant across full and empty AAVs.

Figure 9A:
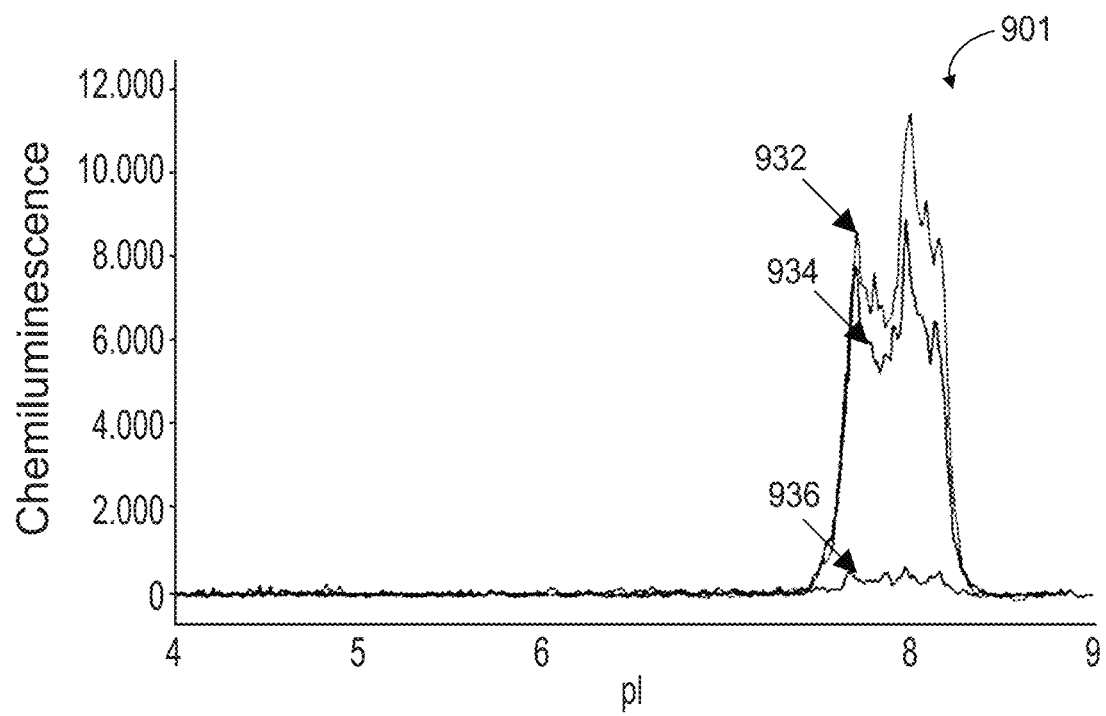
FIGS. 9A and 9B are graphs showing experimentally obtained traces representing signals associated with quantitative analysis of a NA content and a protein content, respectively, in samples containing particles for gene delivery as described herein. Signals shown represent effects before and after treatment of the samples with a buffer and a nuclease.
Figure 9B:
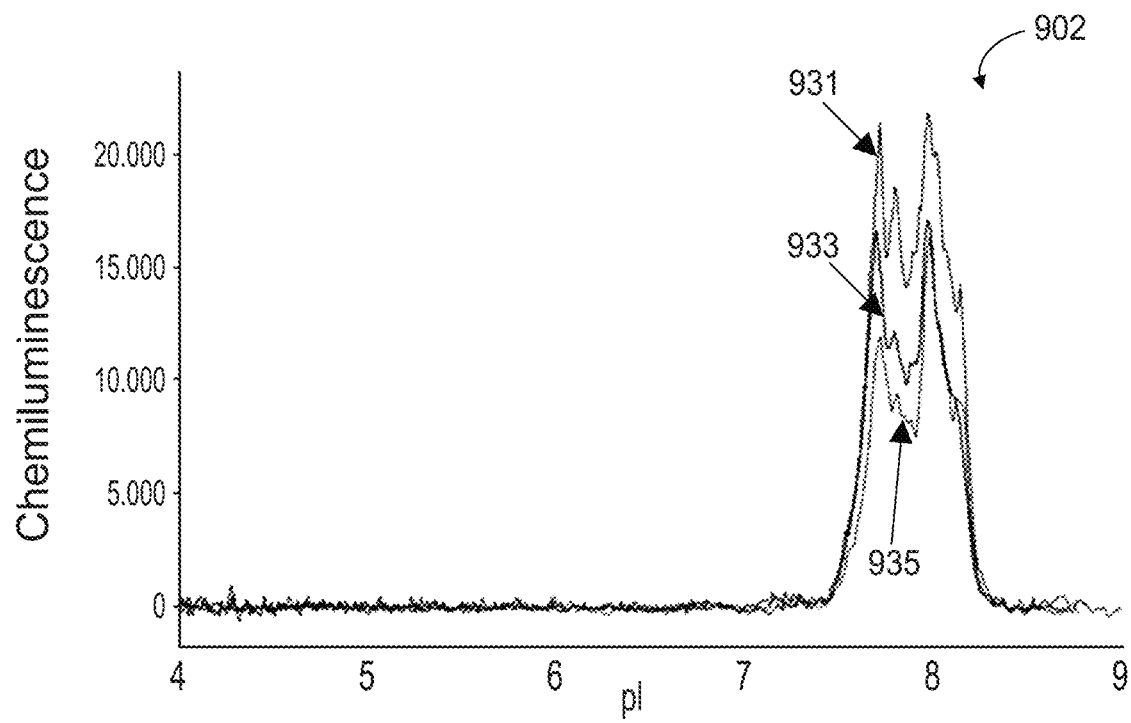

In some implementations, experiments can be conducted to ensure that the signals associated with the NA content are originating from the NA content housed within the GD particles in a sample (and are not free NA content that may be impurities). In some implementations, the sample can be treated with nucleases that are configured to breakdown the NA structure within the GD particles and retesting the sample following the treatment. As a control, the sample can be treated with a buffer that is expected to have no effect on the NA structure. The specificity of the anti-NA antibodies can also be tested following this procedure. For example, the enriched sample containing 77% AAV9 particles in the full state can be treated with nuclease and retested as described above. FIGS. 9A and 9B show the signals associated with NA content and protein content, respectively, obtained from a sample before and after a treatment of nuclease and before and after the treatment of a control buffer. The plot 901 shows signal 932 associated with NA content in a sample, and signal 934 associated with AAV particles after treatment with a buffer, and signal 936 associated with AAV particles after treatment with a nuclease. The plot 902 shows signal 931 associated with protein content in the sample, and signal 932 associated with AAV particles after treatment with a buffer, and signal 933 associated with the AAV particles after treatment with a nuclease. As shown, there is no significant change in signal associated with NA content before and after treatment with a control buffer (compare signals 932 and 934). There is, however, a drastic reduction in the signal compared before and after nuclease treatment (compare signals 932 and 936). The signal indicating presence and/or quantity of DNA is almost eliminated in 936. The signals indicating protein content, however, shown in FIG. 9B, are comparably similar (with no significant reduction in signal) before and after treatment with nuclease (compare signals 931 and 935, for example, protein AUC values are within a factor of two while the DNA AUC value reduces by more than an order of magnitude following the nuclease treatment) just as the signals before and after treatment with a control buffer are comparably similar (compare signals 931 and 933. These results confirmed that the signal associated with NA content originated from the DNA content within intact AAV particles.

In some implementations, the methods and processes described herein can be performed using existing systems similar to ProteinSimple's® Simple Western® instrument. Such instruments can be configured to run western blot analyses in a fully automated manner. For example, such instruments can provide fully automated microfluidic-based (e.g., capillary-based) immunoassays. Some such systems can be capable of combining an immunoassay(s) with separation (e.g., separation based on size, isoelectric point, etc.) similar to traditional gel-based western blots, in a capillary. The sample, separation matrix, stacking matrix, antibodies and reagents can be loaded automatically. The instrument can be operable to aspirate a separation matrix and then a stacking matrix into each capillary. A sample containing a heterogeneous mixture of GD particles can be loaded, and capillaries can be brought into contact with running buffer. Voltage can be applied to enable separation by molecular weight, isoelectric points, or other suitable characteristic. Once the separation is complete, UV light can immobilize the proteins to the capillary wall. Immunoprobing of the components involved (e.g., proteins, NA, lipids, inorganic materials, etc.) can be carried out with selective binders with the GD particles including the components being immobilized and the matrix cleared from the capillary. Signals emitted by the binders can be automatically detected and/or analyzed to determine quantities of the components involved.

While various embodiments have been described herein, it should be understood that they have been presented by way of example only, and not limitation. For example, the GD particles have been described to be probed for protein content (e.g., in capsids of viral vectors) and for NA content (e.g., genetic material carried as payload) by way of example. In some implementations, the encapsulation of the GD particles could be any suitable first component (e.g., lipids) and the payload can include any suitable second component (e.g., xenobiotics, pharmaceutical molecules, proteins, etc.). The GD particles can be probed to detect and/or quantify the first component (e.g., lipids) using binders selective for the first component (e.g., lipid selective antibodies, or phospholipid selective antibodies based on state of phosphorylation, etc.). The GD particles can be probed to detect and/or quantify the second molecule (e.g., therapeutic drug or molecule, protein, etc.) using binders selective for the second component (e.g., antibodies selective for the therapeutic drug or molecule, protein-specific antibodies, biotin, etc.). The first component can be any suitable material that can be used to form a suitable structure that can serve as a carrier (e.g., nanocarriers) for holding (e.g., entrapment, encapsulation, and/or the like) and/or carrying a payload. Some examples of carriers can include polymeric nanoparticles (e.g., nanospheres, nanocapsules, etc.), hydrogel nanoparticles, micelles, lipid nanocarriers, liposomes, phospholipid micelles, metal and/or inorganic nanoparticles (e.g., gold nanoparticles, carbon nanotubes, nanoshells, quantum dots, etc.), magnetic nanoparticles, and/or the like. Some examples of the first component can include organic biomolecules (e.g., proteins, lipids, etc.), inorganic materials (e.g., metal, silica, carbon, polymer, hydrogel, etc.). Some examples of the second component can include therapeutic drugs, pharmaceutical molecules, labeling components (e.g., nanodots), genetic material, xenobiotics, therapeutic or diagnostic products configured for targeted delivery, and/or the like.

Furthermore, although various embodiments have been described as having particular features and/or combinations of components, other embodiments are possible having a combination of any features and/or components.

While various embodiments have been described above, it should be understood that they have been presented by way of example only, and not limitation. Where methods and steps described above indicate certain events occurring in certain order, the ordering of certain steps may be modified. Additionally, certain of the events may be performed repeatedly, concurrently in a parallel process when possible, as well as performed sequentially as described above. Furthermore, certain embodiments may omit one or more described events. Where methods are described, it should be understood that such methods can be computer-implemented methods. Similarly stated, a non-transitory processor readable medium can store code representing instructions configured to cause a processor to cause the described method to occur or be carried out. For example, an instrument, such as ProteinSimple's® Peggy Sue™, can include a processor and a memory and can cause one or more method steps described herein to occur. Thus, some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes.

Although various embodiments have been described as having particular features and/or combinations of components, other embodiments are possible having any combination or sub-combination of any features and/or components from any of the embodiments described herein.

What is claimed is:

1. One or more non-transitory processor-readable media storing code representing instructions to be executed by one or more processors, the instructions comprising code to cause the one or more processors to:
   receive a first test signal associated with a test sample containing a plurality of viral vectors, the first test signal being associated with nucleic acid (NA) included in at least a first subset of viral vectors from the plurality of viral vectors;
   receive a second test signal associated with the test sample containing the plurality of viral vectors, the second test signal being associated with protein included in at least a second subset of viral vectors from the plurality of viral vectors, the first subset of viral vectors and the second subset of viral vectors each being separated in at least one miniaturized fluidic path based on a property of the plurality of viral vectors; and
   determine a proportion of the plurality of viral vectors contained in the test sample that are in a full state based on (1) a first feature of the first test signal, the first feature associated with a quantity of NA associated with the first subset of viral vectors, (2) a first standard signal from a first standard sample that has a known proportion of viral vectors that are in a full, at least partially full and/or empty state, (3) a second feature of the test signal, the second feature associated with a quantity of protein associated with the second subset of viral vectors, and (4) a second standard signal from a second standard sample that has a known proportion of viral vectors that are in a full, partially full and/or empty state.

2. The one or more non-transitory processor-readable media of claim 1, wherein the first subset of viral vectors is the same as the second subset of viral vectors.

3. The one or more non-transitory processor-readable media of claim 1, wherein the first subset of viral vectors and the second subset of viral vectors are located at a common position in the at least one miniaturized fluidic path.

4. The one or more non-transitory processor-readable media of claim 3, wherein the location of the first subset of viral vectors and the second subset of viral vectors in the at least one miniaturized fluidic path is based on at least one of a molecular weight, a size, or an isoelectric point of the first subset of viral vectors and the second subset of viral vectors.

5. The one or more non-transitory processor-readable media of claim 1, wherein the first standard sample is the same as the second standard.

6. The one or more non-transitory processor-readable media of claim 1, wherein the first standard sample and the second standard sample are associated with an identity of the plurality of viral vectors.

7. The one or more non-transitory processor-readable media of claim 6, wherein the identity of the plurality of viral vectors includes a type of virus used to generate the plurality of viral vectors.

8. The one or more non-transitory processor-readable media of claim 1, wherein the at least one miniaturized fluidic path is at least one capillary.

9. The one or more non-transitory processor-readable media of claim 1, wherein the at least one miniaturized fluidic path is at least one microfluidic channel.

10. The one or more non-transitory processor-readable media of claim 1, wherein the plurality of viral vectors comprise a plurality of viral capsids.

11. The one or more non-transitory processor-readable media of claim 1, wherein the instructions further comprise code to cause the one or more processors to:
send a signal associated with the proportion of the plurality of viral vectors contained in the test sample that are in a full state.

12. The one or more non-transitory processor-readable media of claim 1, wherein the first test signal includes data associated with an electrophoretic separation associated with nucleic acid (NA) included in at least the first subset of viral vectors from the plurality of viral vectors, and the second test signal includes data associated with an electrophoretic separation associated with protein included in at least the second subset of viral vectors from the plurality of viral vectors.

13. The one or more non-transitory processor-readable media of claim 1, the instructions further comprise code to cause the one or more processors to:
normalize the first feature using the first standard signal; and
normalize the second feature using the second standard signal,
the proportion of the plurality of viral vectors contained in the test sample that are in the full state is determined based on a ratio of the first feature, after normalization, to the second feature, after normalization.

14. The one or more non-transitory processor-readable media of claim 1, the instructions further comprising code to cause the one or more processors to:
identify the first feature from the first test signal; and
identify the second feature from the second test signal.

15. The one or more non-transitory processor-readable media of claim 1, wherein each viral vector from the proportion of the plurality of viral vectors contained in the test sample that is in a full state includes a desired amount of NA.

16. The one or more non-transitory processor-readable media of claim 1, wherein:
the first standard sample has a known proportion of viral vectors that are in the full state; and
the second standard sample has a known proportion of viral vectors that are in the full state.

17. One or more non-transitory processor-readable media storing code representing instructions to be executed by one or more processors, the instructions comprising code to cause the one or more processors to:
receive a first test signal associated with a test sample containing viral capsids, the first test signal being associated with nucleic acid (NA) included in viral capsids from a first portion of the test sample, the NA included in viral capsids from the first portion of the test sample having undergone electrophoretic separation;
receive a second test signal associated with the test sample containing the viral capsids, the second test signal being associated with protein from viral capsids from a second portion of the test sample, the protein from viral capsids from the second portion of the test sample having undergone an electrophoretic separation;
identify a first feature from the first test signal, the first feature being associated with a quantity of the NA included in viral capsids from the first portion of the test sample;
identify a second feature from the second test signal, the second feature being associated with a quantity of the protein from viral capsids from the second portion of the test sample;
determine a proportion of the viral capsids contained in the test sample that are in a full state based on (1) the first feature, (2) a first standard signal obtained from a first standard sample with a known proportion of viral capsids that are in a full, partially full and/or empty state, (3) the second feature, and (4) a second standard signal obtained from a second standard sample with a known proportion of viral capsids that are in a full, partially full and/or empty state; and
sending a signal associated with the proportion of the viral capsids contained in the test sample that are in a full, partially full and/or empty state.

18. The one or more non-transitory processor-readable media of claim 17, wherein the first standard sample is the same as the second standard sample.

19. The one or more non-transitory processor-readable media of claim 17, wherein the instructions further comprise code to cause the one or more processors to:
receive the first test signal from a device having a miniaturized fluidic path.

20. The one or more non-transitory processor-readable media of claim 19, wherein the identity includes a type of virus used to generate the at least a portion of viral capsids.

21. The one or more non-transitory processor-readable media of claim 17, wherein the instructions further comprise code to cause the one or more processors to:
 send a signal to cause electrophoretic separation of NA included in viral capsids from the first portion of the test sample.

22. The one or more non-transitory processor-readable media of claim 17, the instructions further comprising code to cause the one or more processors to:
 normalize the first feature using the first standard signal; and
 normalize the second feature using the second standard signal,
 the proportion of the viral capsids contained in the test sample that are in the full state determined based on a ratio of the first feature after normalization to the second feature after normalization.

23. The one or more non-transitory processor-readable media of claim 17, wherein:
 the first standard sample has a known proportion of viral vectors that are in the full state; and
 the second standard sample has a known proportion of viral vectors that are in the full state.

* * * * *